United States Patent [19]

Klainer et al.

[11] Patent Number: 5,059,790
[45] Date of Patent: Oct. 22, 1991

[54] RESERVOIR FIBER OPTIC CHEMICAL SENSORS

[75] Inventors: Stanley M. Klainer, Henderson; Chet A. Frank, Las Vegas; Dileep K. Dandge; Kisholoy Goswami, both of Henderson, all of Nev.

[73] Assignee: FiberChem, Inc., Las Vegas, Nev.

[21] Appl. No.: 503,463

[22] Filed: Mar. 30, 1990

[51] Int. Cl.$^5$ ............................................. H01J 5/16
[52] U.S. Cl. ............................ 250/227.21; 128/634; 385/123
[58] Field of Search ............................ 250/576, 227.21; 128/634; 350/96.29, 96.18; 356/39, 40, 41

[56] References Cited

U.S. PATENT DOCUMENTS

| 3,814,081 | 6/1974 | Mori | 128/634 |
| 4,344,438 | 8/1982 | Schultz | 128/634 |
| 4,682,895 | 7/1987 | Costello | 128/634 |

Primary Examiner—David C. Nelms
Assistant Examiner—Shami
Attorney, Agent, or Firm—Henry P. Sartorio

[57] ABSTRACT

Single and multi-cell reservoir FOCS configurations, with single or dual fibers with optional optical elements, have a cross-flow arrangement of the sample relative to the fiber. A wide variety of sensors, including pH, arsenic, benzene, cyanide, hydrazine, cupric ion; TCE, mercuric ion, and iron(2+) are provided.

38 Claims, 30 Drawing Sheets

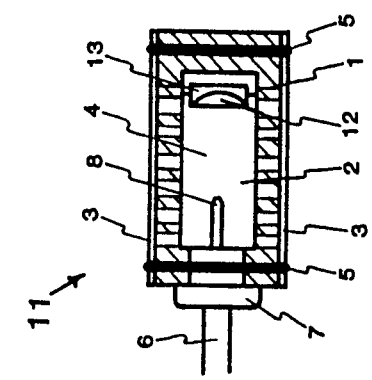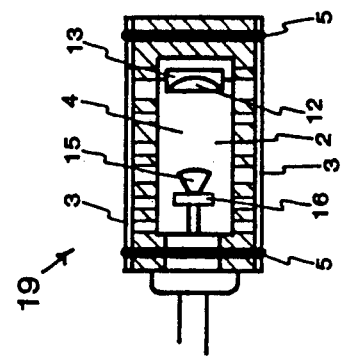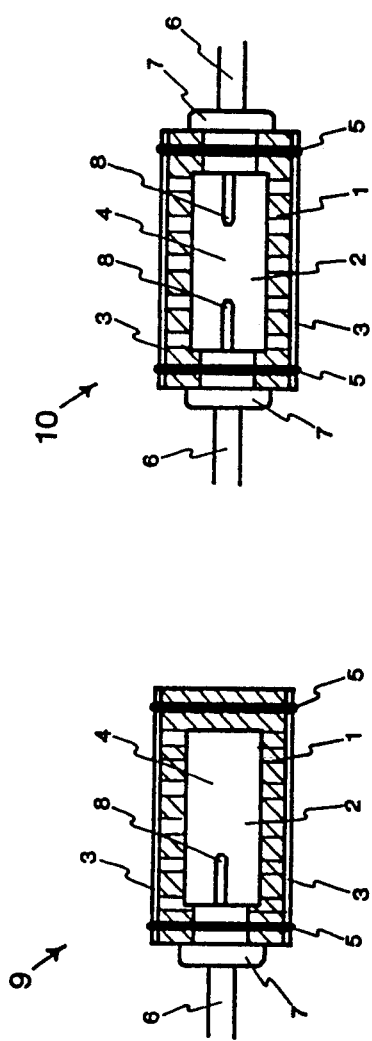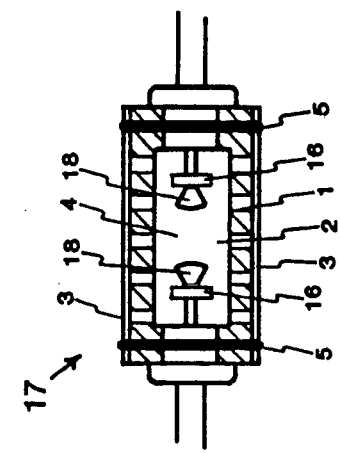

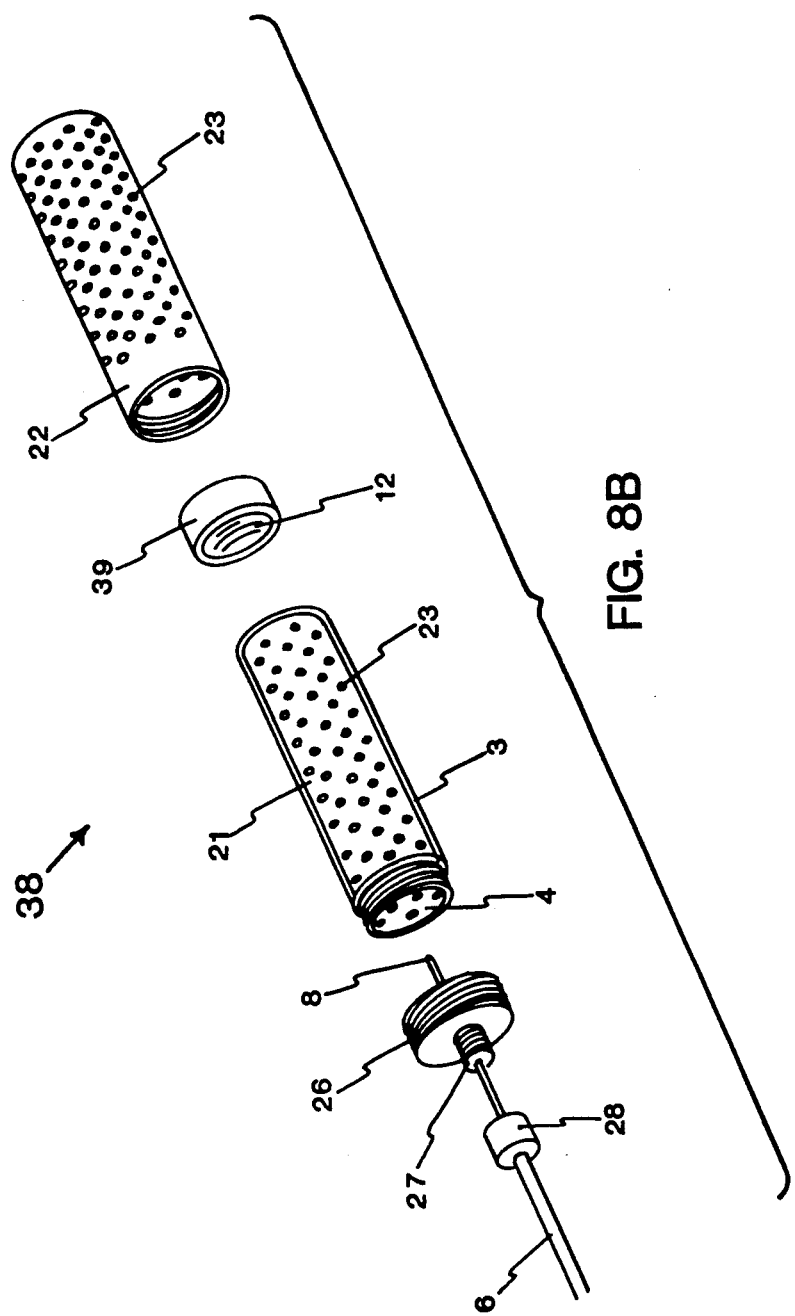

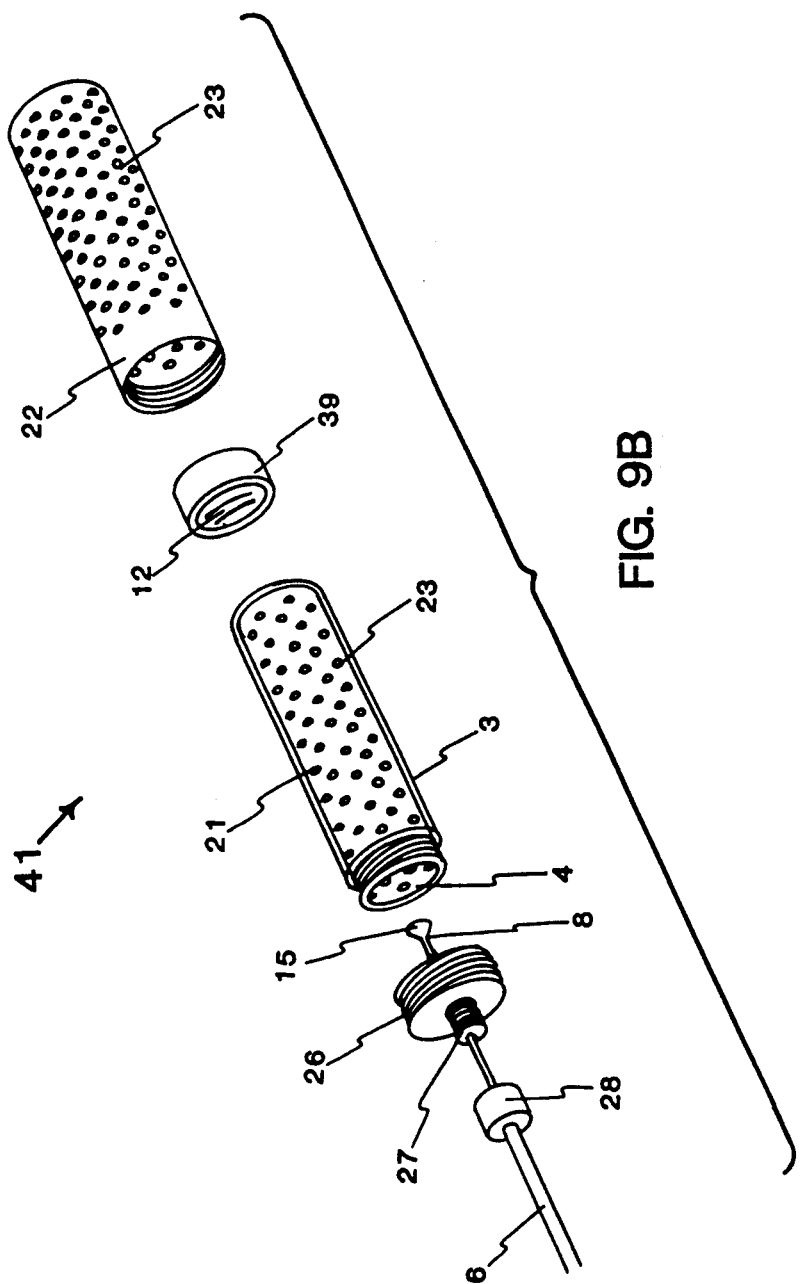

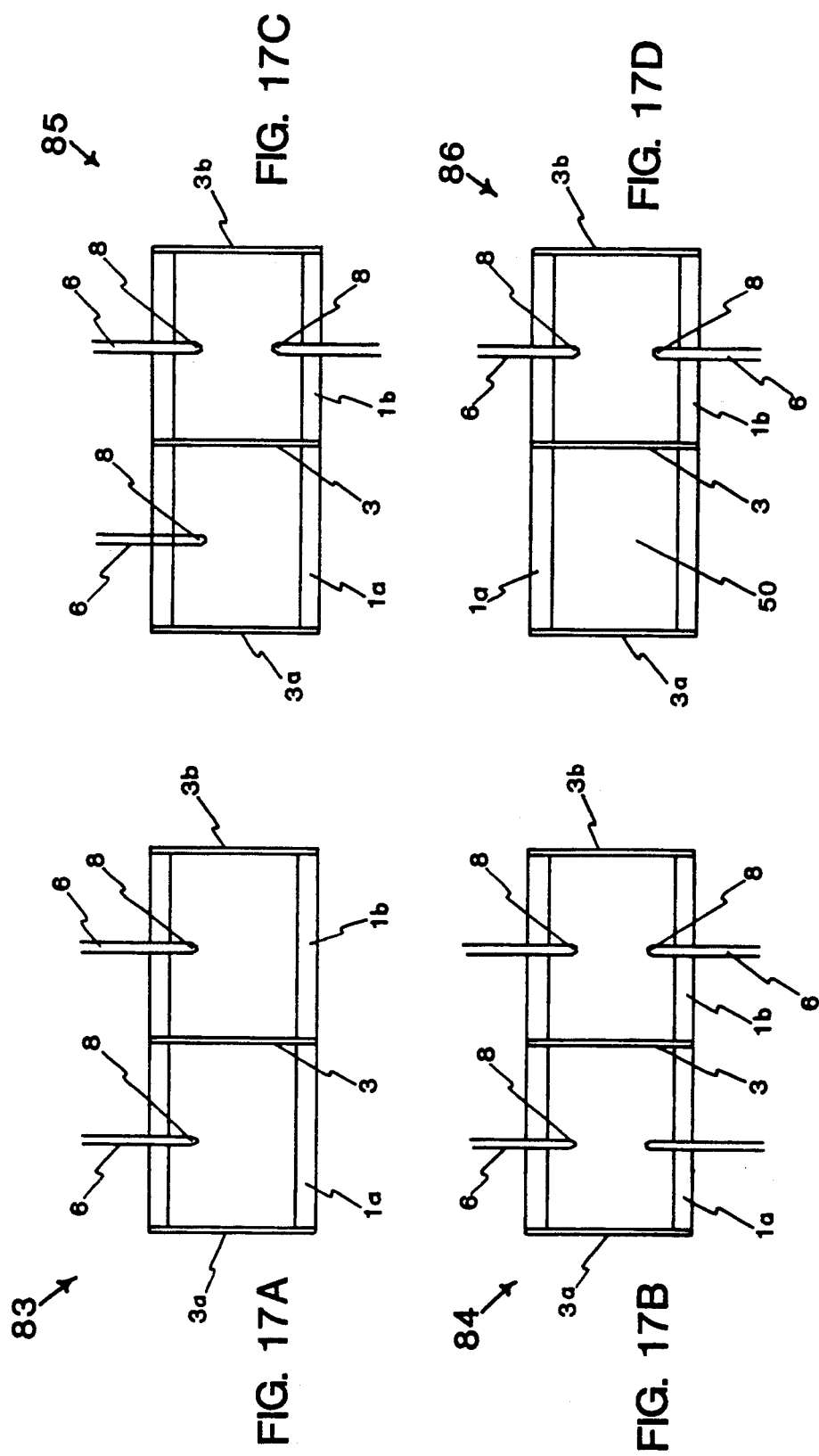

RESERVOIR FIBER OPTIC CHEMICAL SENSORS

BACKGROUND OF THE INVENTION

The invention relates generally to fiber optic chemical sensors (FOCS) and more particularly to reservoir FOCS (e.g., U.S. Pat. No. 4,892,383 to Klainer, et al.), specifically measurement techniques, cell design, construction materials, membrane selection, and applications.

The basic FOCS design is a tip coated FOCS in which a reagent that specifically and sensitively interacts with the analyte of interest is placed or attached at the tip of an optical fiber. Fibers in the 100 to 1,000 micron diameter range are most often used. Unfortunately, because of the very small surface areas at their tips ($8 \times 10^{-5}$ to $8 \times 10^{-3}$ cm$^2$) it is difficult to get enough chemistry at the end of the fiber for reliable measurements, i.e. good signal to noise.

Several approaches have been used to get enough chemistry onto the tip of the fiber and thus overcome the surface area limitations, including: (i) surface amplification techniques, a unique type of covalent immobilization in which the sensing material is attached to the tip by a surface amplification polymer; (ii) imbedding the chemistry into a membrane placed at the tip of the fiber; (iii) large surface area porous glass fibers attached to the tip; and (iv) use of very sensitive chemistry, i.e. fluorescence reactions. In special situations, where the species to be measured is volatile, reservoir FOCS (liquid reagents) with gas permeable membranes have been used. Each of these has shown severe drawbacks. The surface amplification approach works but it is impossible to make several FOCS, either individually or by a batch process, which are similar. Imbedding the chemistry in the membrane results in such disadvantages as slower response times, "leaking" of the reagents and difficulty in making uniform systems. Porous glass fibers, especially the newer ones with the larger pores (>300 $\mu$m), appeared to be a big breakthrough, but the large buffering capacity of the glass is a major problem as is its ability to trap unwanted molecules. The use of fluorophores, in the past, has been considered a drawback because of bleaching problems. Finally reservoir cells have been very difficult to use and to make uniformly, and it is also burdensome to obtain reliable data.

Evanescent wave FOCS and side coated FOCS, particularly the multilayered FOCS where the reacting chemistry is sandwiched between the core and clad as described in U.S. Pat. No. 4,846,548 to Klainer are alternative FOCS designs where the sensing material can be placed on the sides of the fiber.

The need for high resolution, long active lifetimes and good reproducibility between sensors for a particular species indicates the desirability of an improved reservoir sensor. The sensing reagents are in liquid form and kept in the sensor by a species permeable membrane. All of the key elements of the sensor should be very accurately controlled. Ideally, reagent solution can be made with a very high degree of repeatability, the active volume can be precisely controlled, the field-of-view of the fiber is accurately known, and the size and permeability of the membrane can be held to good tolerances. Thus designs are needed which can incorporate all these features and advantages. The big drawback of the reservoir FOCS is size. It is about 1 cm in diameter compared to other FOCS which are 400 to 1,000 $\mu$m.

Thus while reservoir FOCS would be particularly desirable for many applications, including sampling in an aqueous environment, present sensors are inadequate. U.S. Pat. Nos. 4,757,343 to Hirschfeld and 4,666,674 to Miller et al. show typical reservoir FOCS formed by attaching a capillary tube coaxially to the end of an optical fiber using a gas bubble or membrane to close the tube. This structure is difficult to assemble accurately, difficult to control and use and impossible to reproduce uniformly. Another type of FOCS, while not actually a reservoir type, is shown by U.S. Pat. No. 4,478,872 to Peterson et al. wherein a porous polymer jacket or envelope is placed at the end of a pair of fibers and encloses a fluorescent dye on a solid (particulate) support.

U.S. Pat. No. 4,892,383 to Klainer, et al provides an improved reservoir FOCS having a modular design. A modular reservoir cell body has an optical fiber precisely positioned in one end by means of a quick connect fiber optic connector and a semi-permeable membrane attached across the opposite end by a quick connect membrane retainer. While this design overcomes many of the prior problems, the design is not optimally suitable for all applications. The width of the cell body limits the size of the membrane which is the surface through which the species of interest passes into the cell. The material that flows into the cell leaves the cell by a reverse flow through the membrane. The fiber may only be positioned at one end of the cell. A more versatile configuration with larger membrane area, better flow characteristics and more flexibility in optical fiber arrangement would be desirable.

The ability to detect or monitor trace amounts of chemical species in situ is of great importance and generally difficult to do. Particular applications include environmental monitoring, pollution control, process control, public health and safety, clinical medicine and industrial monitoring. Groundwater, seawater and atmospheric (air) monitoring are very important. The improved reservoir FOCS would be particularly desireable for many of these applications.

The safety of drinking water and the ability of both sweet and sea water to support plant and animal life has become one of the world's key concerns. This, added to the already recognized air pollution problem further complicates the need for monitoring and corrective action. The list of substances that are to be monitored continually increases while, as clinical evaluations continue, the MAC (maximum acceptable concentration) is constantly decreasing. This means that the burden placed on analytical methods is quickly exceeding available specificity and sensitivity. Furthermore, as the accountability for analytical data becomes more demanding, the complexity of the instrumentation and the time to perform an analysis escalates accordingly. When these requisites are considered in light of the fact that there are hundreds of inorganic, organic and biological compounds that are potentially dangerous, toxic or carcinogenic and that there are also supplementary requirements such as pH, turbidity and the amount of coliform bacteria, the need for a simple method of analyses which can be adapted to many of the targets of interest becomes obvious.

The importance of safe and plentiful ground water supplies cannot be overstated. Domestic water quality is being threatened in many areas by the intrusion of toxic contaminants into the soil and the ground water from agricultural runoff of pesticides and herbicides; industrial discharge into lakes and rivers; and seepage from solid waste sites (landfills, storage lagoons, and waste piles). Unlike surface contaminants, which are quickly diluted, chemicals in the soil and ground water often remain highly concentrated both underground and in the water which flows from the faucet. The potential magnitude of the problem is enormous. It is, therefore, essential that an economical, practical water monitoring system be in place as soon as possible.

In order to provide adequate protection of water sources, methods of detecting low concentration of toxic contaminants are urgently needed. This includes measuring inorganic, organic and biological species. The public health, as well as the public's confidence in domestic water supplies, requires an early warning system so that prompt action may be taken to track down the sources of the contamination and to take appropriate steps to protect the public. In order to assure soil and water quality, the contaminants must first be identified. Presently, sophisticated state-of-the-art equipment and methodologies have been used for diagnostic investigation. Wells sometimes must be drilled for proper access to the vadose zone and ground water. Typically, gas chromatography and mass and atomic (absorption and emission) spectroscopy have been used in conjunction with special pumps and samplers to collect the soil and water to be analyzed. Unfortunately, present technologies are not suitable for continuous and widespread monitoring of groundwater contamination. Problems include the contamination of samples by well construction materials, degradation of sample integrity by most sampling techniques which could result in questionable data and make enforcement difficult, the high capital investment in complex equipment, and the need for highly skilled technicians. An improved reservoir FOCS which is accurate and uniform over a large number of sensors should be the basis of an acceptable, practical monitoring system.

The growing concern over depleted levels of oxygen and increasing levels of carbon dioxide and other trace gases on a global scale has warranted the need for improved methods for oceanic and atmospheric gas analysis and monitoring. The ocean flux process permits carbon dioxide to escape from the ocean and depleted oxygen to be replenished. According to recent predictions, "greenhouse" gases in the atmosphere are on a continuous rise and will result in a global warming of as much as 2° to 3° C. in the next 50 years.

The need for in situ monitoring of key chemical components in seawater is becoming increasingly more apparent. To develop a better understanding of the parameters which affect ocean flux requires measuring key chemical species as they simultaneously exist in order to obtain time series data. These components are currently measured by collecting water at the site using specially designed water samplers operated from a manned submersible or remotely operated vehicle. These samplers are made of titanium, are expensive, and time consuming to clean and maintain. The water samples are then brought to the surface and analyzed by conventional laboratory techniques to determine the results. FOCS have the potential to satisfy this monitoring need, which is unattainable with existing instrumentation.

There are presently a very limited number of FOCS systems available for commercial use in aqueous systems and virtually none available for use in seawater. Present day methods for the direct measurement of specific chemical parameters in seawater include deployed seawater probes for dissolved oxygen and pH that are based on electrochemistry. These Clark-type probes work either on the galvanic or polarographic principle and have a number of problems including slow response time, reproducibility, chemical and biological fouling of protective membranes, and other effects of high salinity on sensor performance and sensor lifetime. Fiber optic chemical sensors can overcome these problems and will offer many advantages, including batch fabrication at reasonable cost, expendability, small size, light weight and freedom from electromagnetic interference. In FOCS, signals are transmitted optically rather than electrically, which becomes advantageous when handling and deploying long lengths of sea cable in electrically noisy shipboard environments. A reservoir FOCS adapted to these types of measurements will make a groundwater or seawater monitoring system feasible.

Acidity (pH) of surface and ground water is caused by humic acid extracted from swamps or peat beds and by industrial pollution. Excessive acidity causes corrosion which results in many undesirable species entering into the water such as iron, lead and zinc and can be detrimental to fish life. A pH of 6.0–8.5 is both permissible and desireable in sweet water and 7.0 to 9.0 in sea water.

Arsenic in water is of great concern. Severe toxicity can exist after the ingestion of less than 100 mg of arsenic and chronic toxicity develops with even lower intakes. Arsenic enters the water system either from geological sources as arsenate and arsenite but it is industrial discharge that increases the arsenic content above safe levels. Although 0.1 ppm is the MAC (maximum allowable concentration) for arsenic, "virtually absent" is the desired level.

Bacteria count is used to determine the sanitary quality of water. Coliform bacteria are normally present in feces, soil and vegetation. It is important to distinguish between fecal and non-fecal coliform since it is the fecal species that is disease producing. The presence of more than 10,000 coliforms per 100 milliliters of water indicates a recent, and possibly dangerous, pollution event.

Benzene is one of the most dangerous toxicants. Not only is it a known carcinogen, but it also can cause irritation of the mucous membranes, convulsions and mood changes. Benzene sources include cigarettes, automobile fuels, and industrial processing. The result can be death from cancer or respiratory failure or blood disease. The MAC of 0.005 ppm is probably too high and complete absence is desirable.

Carbon dioxide has to be measured if there is any hope of understanding the ocean flux process. An in-situ measurement capability for dissolved carbon dioxide in the ocean is an important first step toward understanding the ocean flux process. This capability is needed by researchers engaged in ocean and global climate studies.

Chromium in drinking water is of concern because it is a suspected carcinogen. Chromium exists in two valence states, 3+ and 6+. Of these chromium (6+) is by far the most dangerous. It enters the drinking water from cooling towers, waste water plants, plating operations and the tanning industry. Although the MAC for chromium (6+) is 0.05 ppm, its presence in drinking water above 0.003 ppm indicates the presence of industrial pollution. The complete absence of chromium is the desired level.

Copper content in water should be "virtually absent", although some small amount, 0.1 ppm, is needed for plant growth and body metabolism. If copper is totally absent from drinking water, nutritional anemia may appear in children. Concentrations greater than 0.1 ppm, on the other hand, diminish algae and plankton growth, but at the same time are toxic to several species of fish.

Cyanide is toxic to aquatic organisms at even the lowest levels. The toxicity is due to the liberation of hydrocyanic acid which inhibits oxygen metabolism. Natural waters do not contain cyanide. It comes, primarily, from industrial applications such as metal cleaning and electroplating baths, gas scrubbers and chemical synthesis. The MAC is 0.01 ppm but the desired level is absent.

Hydrazine is a violent poison having a strong caustic effect on the skin and mucous membranes. It can lower the metabolism by upsetting certain enzyme systems. The MAC for hydrazine is 5 ppm with a desireable limit of <0.5 ppm.

Iron is not a potential health hazard but it has the ability to cause pipe encrustation and it causes aesthetic problems, i.e., rust spots on clothing and rust stains in sinks. It also makes the taste of drinking water objectionable. Iron enters the water system by leaching from natural iron deposits or from iron-containing industrial wastes. The soluble form is iron $(2+)$ and the insoluble one iron $(3+)$. The allowable limit is 0.1 ppm iron $(2+)$ and 0.2 ppm iron $(3+)$. The desired level is "virtually absent".

Lead in drinking water arises from many sources such as lead pipes and plastic pipes stabilized by lead. It is toxic to aquatic organisms and accumulates in the human bone structure when more than 300 micrograms per day are ingested. In many situations the actual concentration of lead present is masked by the precipitation of lead chloride and lead carbonate. The allowable lead concentration is 0.05 ppm with absent being the desired level.

Mercury may cause nausea, abdominal pain, vomiting, diarrhea and headache. Continuous exposure to mercury could result in inflammation of the mouth and gums, kidney damage, spasms and a change of personality. The MAC is 0.1 ppm with "virtually absent" being the desired level.

Nitrate in water indicates the final stage of water decomposition. High levels of nitrates may indicate biological waste material in the final stages of stabilization or contamination from the run off of agricultural fertilizers. Nitrate also enhances the excessive growth of algae. Since nitrite is changed to nitrates by certain bacteria, the MAC of 10 ppm is for the total nitrate/nitrite concentration. Amounts greater than this can cause moglobemia in infants ("blue babies"). The desired level is "virtually absent".

Oxygen is one of the most important measurements in both sweet and sea water because dissolved oxygen is the best water quality indicator. Dissolved oxygen (DO) is necessary to support all life in the marine environment and is, therefore, the most important water quality parameter. DO concentration is controlled by a process known as oxygen demand. Oxygen demand materials require oxygen for degradation which results in a depletion of ambient DO levels, thereby depriving marine organisms. Man made wastes, such as sewage sludge and other forms of organic wastes, are examples of oxygen demand materials. These wastes are also known to cause increased nutrient loading resulting in excessive marine plant growth. It is therefore essential to control the amount and type of waste materials dumped into marine waters and to routinely measure and monitor dissolved oxygen to ensure that adequate levels are available to support marine life. Conditions of low dissolved oxygen often occur in highly populated estuarine and coastal areas. Drinking and industrial water should contain at least 4 ppm oxygen but, in general this must be higher to sustain aquatic life. 8–15 ppm is adequate in both sweet and sea water while air-saturated oxygen is the desired level.

Phosphate is important because in excess it leads to atrophy in lakes. It is also necessary to monitor for phosphate in boiler and cooling towers because it encrusts on the walls. Phosphate gets into the water system from agricultural run off, biological waste, corrosion control materials, detergents and surfactants. The MAC is 50 ppm. Inorganic phosphate must be distinguished from the very toxic organic phosphates which are present in pesticides and chemical agents. These are enzyme inhibitors and can cause death. The MAC for organic phosphates is 0.1 ppm with completely absent being the desired level.

Selenium is extremely toxic to humans and animals. It causes inflammation of the lungs and disturbs the digestive and nervous systems. Selenium is a known carcinogen. Its main sources in water are industrial waste and the dissolution of selenium-containing soils. The MAC is 0.01 ppm with complete absence being desireable.

Sulfates themselves are not toxic. They do, however, increase the solubility of other very toxic compounds such as lead. They may also lead to diarrhea by forming the laxatives magnesium and calcium sulfates. The MAC for sulfate is 250 ppm with <50 ppm being desireable.

Sulfides are extremely toxic, especially hydrogen sulfide gas. Collapse, coma, and death from respiratory failure can occur within seconds of its intake. It is as toxic as hydrogen cyanide. Fortunately, its obnoxious odor is detectable long before toxic levels are reached. From a pollution stand point hydrogen sulfide is the by-product of the anaerobic decomposition of organic matter and indicates serious water contamination. The MAC is 0.01 ppm with complete absence being the desired amount.

Sulfur dioxide irritates the respiratory system and could cause bronchitis and asphyxia. It may also be an eye irritant causing conjunctivitis. The MAC is 10 ppm with <0.1 ppm being desireable.

Trichloroethylene (TCE) heads the U.S. Environmental Protection Agency (EPA) list of hazardous (toxic, carcinogenic, etc.) compounds and the organic chlorides, as a group dominate the top ten (10) most frequently found dangerous compounds. TCE is of particular concern because it forms the carcinogen vinyl chloride in water. Moreover, it is estimated that about 23 million people in the United States are exposed each year to TCE levels ranging from 0.5 to 5 ppm even though 0.005 ppm is the MAC and absent is the desired concentration.

The EPA has requirements or is formulating regulations that will require that the above species, as well as others not listed, be continuously monitored. To accomplish this task requires that a device be developed that is both inexpensive to purchase and operate and that can give reliable results in the hands of a moderately trained field technician. Thus the ability to perform the monitoring task (qualitatively and quantitatively) is significant.

SUMMARY OF THE INVENTION

Accordingly, it is an object of the invention to provide improved reservoir FOCS.

It is an additional object to provide reservoir FOCS which can be used with fluorescence, absorption, reflection and refraction techniques.

It is also an object of the invention to provide improved reservoir FOCS designs which are easy to assemble and which can be reproduced substantially identically in multiple sensors.

It is further an object to provide FOCS cell designs which can be made out of metal, polymers (plastics), ceramics and glass.

It is an additional object to make FOCS with membranes whose performances are defined by pore size, molecular weight, surface charge, chemical composition or combinations of these.

It is a further object to make FOCS which have several reaction chambers separated by membranes so that the sample can react with one or more sensing reagents.

It is an additional object to make FOCS which have sample preparation chambers to modify the sample before analysis.

It is another object to construct FOCS out of materials which are biocompatible and/or antifouling.

It is an additional object of the invention to provide reservoir FOCS for detecting and quantifying gases, vapors and dissolved solids.

It is another object to provide reservoir FOCS for detecting and quantifying inorganic species such as cations, anions and non-ionic species, including the differentiation between valence states such as chromium (3+) from chromium (6+) and iron (2+) from iron (3+).

It is a further objective of the invention to provide reservoir FOCS for detecting and quantifying organic species and pharmaceutical products such as compounds, structure and functional groups, including the differentiation between isomers and homologs.

It is an additional objective of the invention to provide reservoir FOCS for detecting and quantifying biological species such as compounds of clinical interest, viruses, bacteria, antigens and enzymes.

The invention includes a reservoir FOCS formed of a modular lateral passthrough reservoir cell body; precision fiber optic connectors, or the equivalent, which are easily attachable to one or both ends and/or one or more sides of the cell body for holding optical fibers precisely positioned within one or both ends and/or one or more sides of the cell body; a species permeable sensing reagent impermeable membrane which covers the lateral surface of the cell body (and optionally an open end); and membrane retainers which are attached to the cell body for holding the membrane in place. The modular cell holds a precise and predetermined amount of liquid reagent. The membrane holds the reagent in the cell and, at the same time, passes the chemical species of interest through the large lateral surface into the cell to interact with the reagent. The fiber optic receives a signal from the reaction, e.g. fluorescence, absorbance, reflection or refraction. Optical focusing and/or collimating elements such as lenses, mirrors or Winston cones can be easily positioned within the cell, at one or both ends, to focus light from the cell volume into the fiber, thereby increasing sensitivity. A flow channel may also be provided along the membrane covered lateral surface of the cell.

The invention also includes FOCS cell designs whereby the species of interest can be pretreated prior to actual analysis. Pretreatment can include creating an excited state, photolysis, radiation, oxidation, reduction, and chemical reactions. This is accomplished by using a flow through chamber placed at the input membrane to the reservoir FOCS. The fiber optics are connected to the cell in an orientation which is substantially orthogonal to the direction of flow through the cell. The flow chamber has inlet and outlet means for flowing, pumping or sucking a gas or liquid sample through the chamber. Excitation, radiation and/or photolyzing sources can be directed into the pretreatment chamber. Reaction chemistries can be placed in the chamber by attaching them to substrates, made of materials such as metal, glass, ceramics and polymers which will not move in the flowing sample stream. The products which result from the reaction of flowing sample with the reactants pass through the membrane and are detected in the reservoir FOCS. The products can flow on through and exit the reservoir cell through an opposed membrane. A multi-cell configuration in which a plurality of chambers are stacked in series, separated by membranes, can be used.

BRIEF DESCRIPTION OF THE DRAWINGS

In the accompanying drawings:

FIGS. 1A-F show six (6) basic reservoir FOCS designs.

FIG. 1A shows a basic single fiber optic system.

FIG. 1B shows a basic two (2) fiber optic system.

FIG. 1C shows a basic single fiber optic system with a focusing mirror.

FIG. 1D shows a single fiber optic system with a lens to increase its field-of-view.

FIG. 1E shows a two (2) fiber optic system with collimating lenses to optimize the sample area viewed and light projection and collection.

FIG. 1F shows a single fiber system with a lens and focusing mirror to increase the observed sample volume and to improve light collection.

FIG. 10A is a two (2) fiber optic system and FIG. 10B is a single fiber optic system.

FIGS. 11A,B are perspective and sectional views of a two (2) fiber optic system.

FIG. 12A is a two (2) fiber optic system and FIG. 12B is a single fiber optic system.

FIGS. 17A,B,C, show three (3) basic designs for multi-cell reservoir FOCS.

FIG. 17A shows a two-cell reservoir FOCS each of which uses a single fiber optic.

FIG. 17B shows a two-cell reservoir FOCS each of which uses two (2) fiber optics.

FIG. 17C shows a two-cell reservoir FOCS one of which uses a single fiber optic and the other two (2) fiber optics.

FIG. 17D shows a two-cell system in which one (1) (or more) cell is a reaction chamber and one cell is a FOCS.

FIG. 18A shows a single cell without membrane.

DETAILED DESCRIPTION OF THE PREFERRED EMBODIMENTS

Figure 2A:
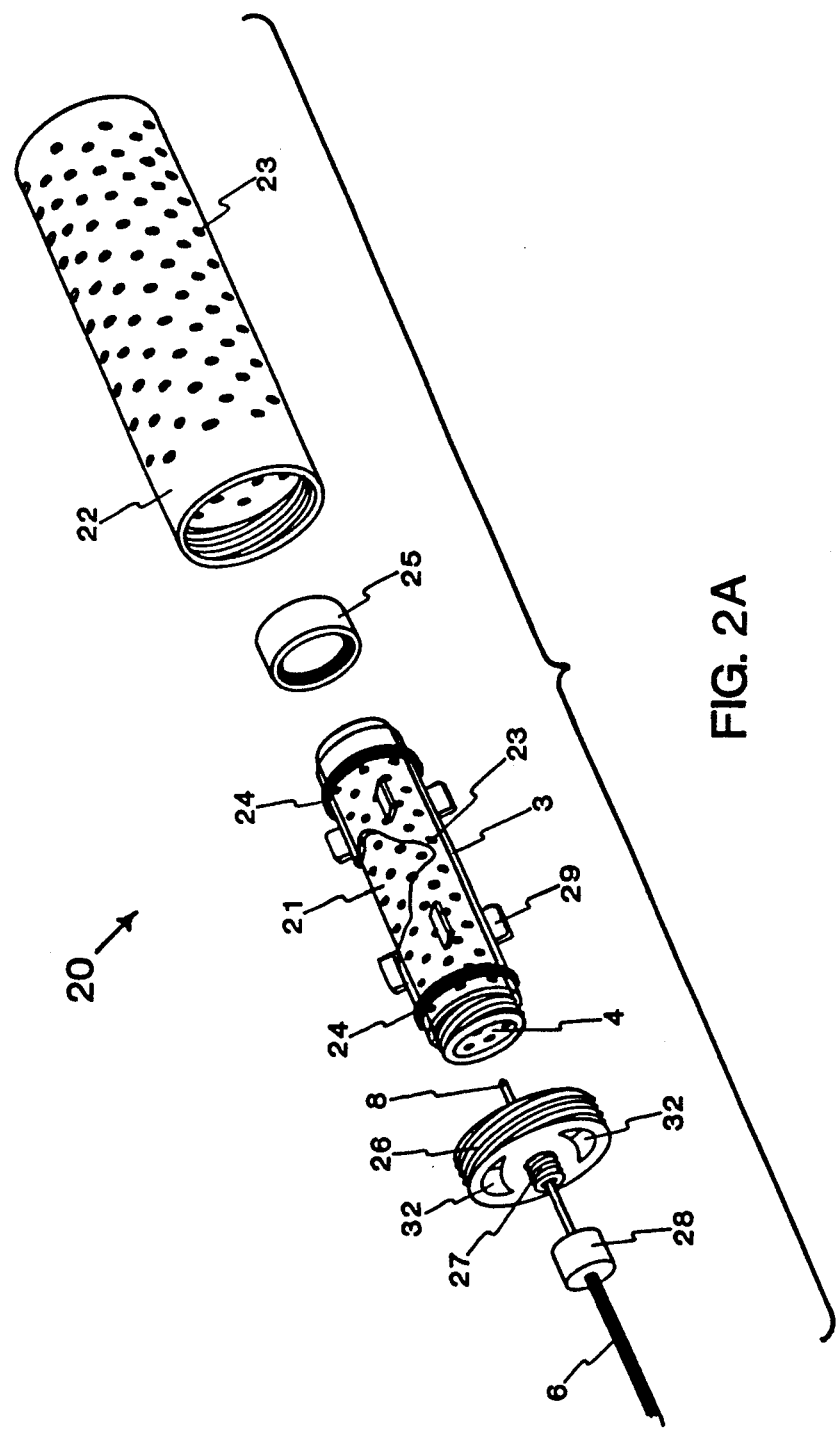
FIGS. 2A,B,C show exploded and assembled perspective views and a sectional view of a modular single fiber reservoir FOCS for the analysis of water or other liquid samples.

As shown in FIG. 1A, a single fiber reservoir FOCS 9 is formed of a lateral passthrough modular reservoir cell body 1. The lateral surface of cell body 1, which is typically cylindrical but may be other shapes, allows liquids and gases to pass therethrough, e.g., it is porous or has holes formed therein, as will be further shown with reference to later figures. A channel 2 or reaction chamber formed in the cell body 1 is filled with a species specific reagent 4. The cell body 1 is covered with a membrane 3 which allows the species to be analyzed to enter the cell while keeping the species specific reagent 4 within the cell. Membrane 3 may also optionally cover the end of cell body 1 opposite the fiber optic 6, or the end may be suitably sealed. Retaining rings 5 hold the membrane 3 in place and effect a liquid tight seal between the cell body 1 and the membrane 3. The fiber optic 6 is placed in the cell 1 through a fiber optic mount 7 which centers the fiber optic 6 within the cell body and makes water tight seals between the fiber optic 6 and the mount 7 as well as the mount 7 and the cell body 1. The reservoir FOCS, as assembled, encloses a predetermined volume which typically contains a known quantity of liquid reagent 4 within the cell body. The measurement volume is defined by the numerical aperture of the fiber optic 6 and the geometry of channel (chamber) 2. The desired chemical species permeate through membrane 3 into channel 2 of cell body 1, interact with reagent 4, and produce an effect, e.g. fluorescence, absorption reflection or refraction, which is detected by the fiber optic 6 through the exposed tip 8 positioned in the cell body. The detection apparatus and light sources required to operate the reservoir FOCS are known in the art and are shown schematically by source/detector assembly 56, FIG. 15 which is positioned at the other end of optical fiber 6 from reservoir FOCS 9. The source may be a laser or lamp which provides an excitation or input optical signal to the reservoir FOCS 9 through fiber optic 6. The reservoir FOCS 9 may be a fluorescence cell or absorption cell or any other known type of cell which produces a detectable optical signal which is transmitted back through fiber 6 to assembly 56. Assembly 56 contains a suitable detector as well as a beam splitter, optical filters and other optics necessary to separate the return signal from the input signal.

The various reservoir FOCS embodiments shown in FIGS. 1B–F all use a similar cell body 1 as used in the simple embodiment of FIG. 1A. The main differences are the addition of a second optical fiber and/or other optical components within the cell. However, the lateral passthrough cell body 1 with membrane 3 mounted on at least the lateral surface of the cell is a key feature of all the cell embodiments.

As shown in FIG. 1B, a two fiber reservoir FOCS 10 is formed which is similar to single fiber reservoir FOCS 9, FIG. 1A, except that reservoir FOCS 10 uses two fiber optics 6 and two fiber optic mounts 7, one at each end of cell body 1. The fiber optics mounts 7 center the fiber optics 6 within the cell body and align the fiber optics 6 opposite each other. The reservoir FOCS, as assembled, encloses a predetermined volume which typically contains a known quantity of liquid reagent 4 within the cell body. The measured sample volume is defined by the volume describe by the numerical apertures of the fiber optics 6. The detection apparatus and light sources required to operate the reservoir FOCS are known in the art and are shown schematically by source/detector assembly 82, FIG. 16 which is positioned at the other end of optical fiber 6 from reservoir FOCS 10. Assembly 82 contains an appropriate source and suitable detector as well as optical filters and other optics necessary to measure the intensity of the return signal.

As shown in FIG. 1C, a single fiber reservoir FOCS 11 is formed which is similar to reservoir FOCS 9, FIG. 1A, except that reservoir FOCS 11 uses a focusing mirror 12 to focus the return light into the fiber to improve light collection efficiency. The focusing mirror is mounted on a focusing plate 13 which permits the position of the focus of the mirror 12 to be optimized relative to the fiber tip 8. The measured sample volume is defined by the circular cone describe by the tip 8 of the fiber optic 6 and the diameter of the mirror. The detection apparatus and light sources required to operate the reservoir FOCS are known in the art and are shown schematically by source/detector assembly 56, FIG. 15 which is positioned at the other end of optical fiber 6 from reservoir FOCS 11.

As shown in FIG. 1D, a single fiber reservoir FOCS 14 is formed which is similar to reservoir FOCS 9, FIG.

1A, except that reservoir FOCS 14 uses a diverging lens 15 to increase the size of the beam coming out of the fiber giving a larger field-of-view than that subtended by fiber tip 8 and this results in a larger measurement volume. The lens 15 also improves light collection efficiency. The lens 15 is attached to the fiber optics by a lens mount 16 or an optical cement. The measured sample volume is defined by the characteristics of the lens. The detection apparatus and light sources required to operate the reservoir FOCS are known in the art and are shown schematically by source/detector assembly 56, FIG. 15 which is positioned at the other end of optical fiber 6 from reservoir FOCS 14.

As shown in FIG. 1E, a two fiber reservoir FOCS 17 is formed which is similar to reservoir FOCS 10, FIG. 1B, except that reservoir FOCS 17 uses collimating lenses 18 to increase the size of the beam coming out of the fiber and make it parallel to the sides of the channel 2. This results in a larger measurement volume and improves light collection efficiency. The lenses 18 are attached to the fiber optics by a lens mount 16 or an optical cement. The measured sample volume is defined by the cylindrical shape subtended by the lenses. The detection apparatus and light sources required to operate the reservoir FOCS are known in the art and are shown schematically by source/detector assembly 82, FIG. 16 which is positioned at the other end of optical fiber 6 from reservoir FOCS 17.

As shown in FIG. 1F, a reservoir FOCS 19 is formed which is a composite of reservoir FOCS 11, FIG. 1C and reservoir FOCS 14, FIG. 1D. Reservoir FOCS 19 uses both an expansion lens 15 and a focusing mirror 12 to optimize both the size of the measurement volume and improve light collection efficiency. The lens 15 is attached to the fiber optic by a lens mount 16 or an optical cement. The mirror is mounted on a focusing plate 13. Measured sample volume is defined by the diameters of the lens and the mirror. The detection apparatus and light sources required to operate the reservoir FOCS are known in the art and are shown schematically by source/detector assembly 56, FIG. 15 which is positioned at the other end of optical fiber 6 from reservoir FOCS 19.

Figure 2B:
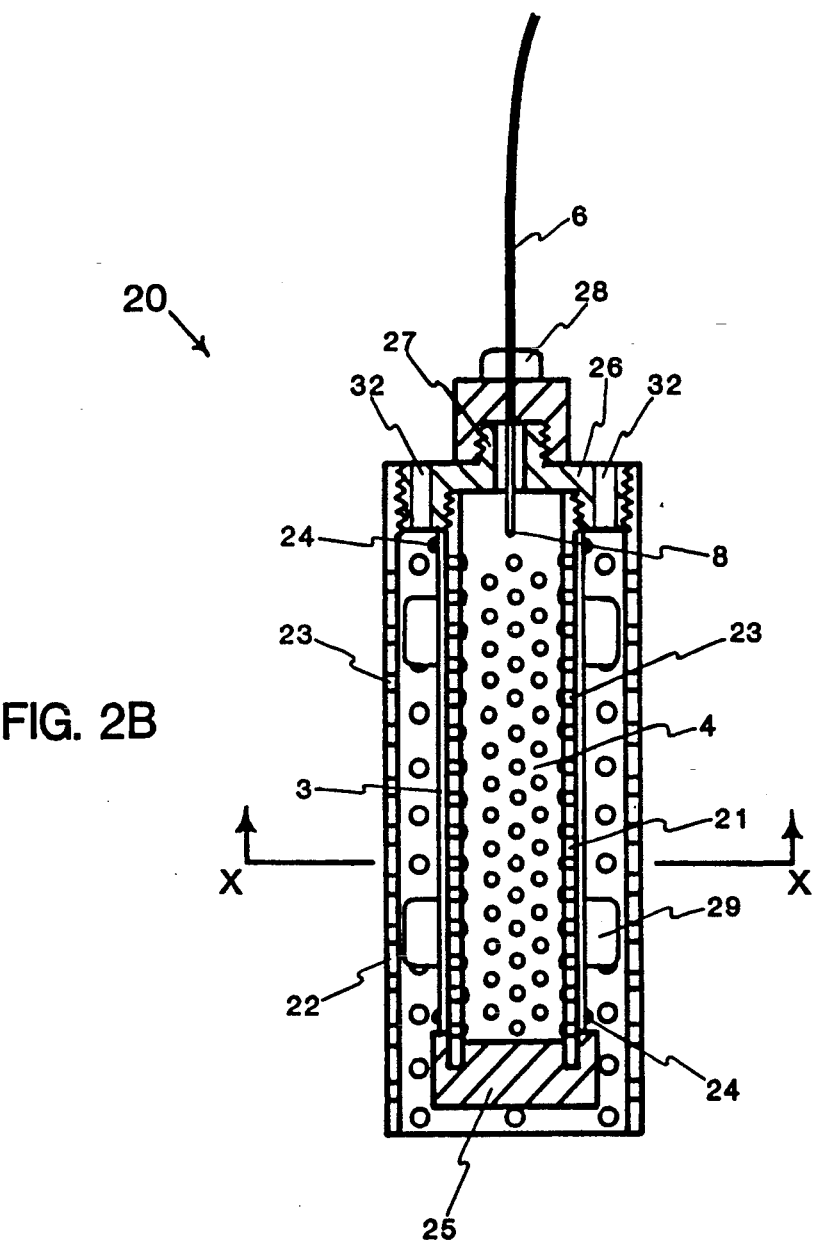
Figure 2C:
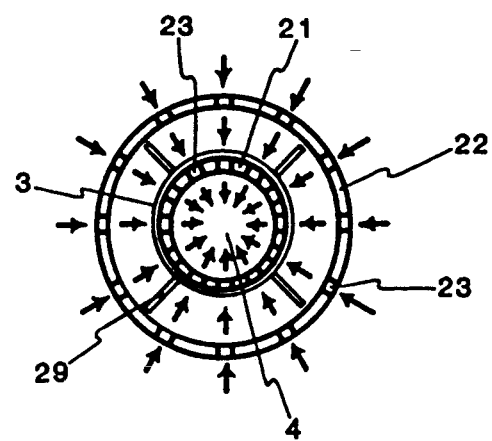

As shown in FIGS. 2 A,B,C a reservoir FOCS 20 can be constructed for water or other liquid analysis. FIG. 2A is an exploded view of reservoir FOCS 20. The design incorporates the use of an inner sleeve 21 and an outer sleeve 22. These sleeves 21,22 have large holes 23 so that water containing the species to be measured can come in contact with the membrane 3 so the species can pass through the membrane and reach the sensing reagent 4. The membrane 3 is tightly wrapped around the inner sleeve 21 and held in place with either "O" rings or plastic straps 24. (In this and other figures, membrane 3 may be shown partly cut-away for clarity.) A liquid tight cap 25 is used to close off the bottom (end that does not have the fiber optic) of the sleeve 21. This cap 25 also is used to seal the edges of the membrane 3 so that liquid can neither seep in nor out of the sensor around the membrane edge. The membrane 3 covered cylinder 21 with one end closed is placed upright and filled with the sensing reagent 4. The tri-purpose top cap 26 is used to effect another liquid tight seal at the top of sleeve 21. The top cap 26 also is used as a support to which the top of the outer sleeve 22 can be attached. The cap 26 contains an adapter 27 so that a liquid tight seal is provided when the fiber optic 6 in its connector 28 is inserted into the cell. The tip 8 of the fiber optic 6 is positioned in the inner sleeve 21 so that it is in the sensing solution 4. Channel holes 32 are provided in top cap 26 so that the liquid sample can flow through the annular region defined between inner sleeve 21 and outer sleeve 22. The relative spacing between the inner and outer cylinders 21,22 is critical because it is important to assure that transport through the membrane remains the rate limiting factor, i.e., that the rate the water reaches the membrane 3 is not retarded. This spacing is controlled by the diameter of cap 26 and spacers 29 which keep the inner and outer sleeves 21,22 accurately separated. The spacers 29 also keep the membrane 3 taut. The spacers 29 provide a liquid channel between the two (2) sleeves 21,22 and are spaced in such a way that they do not impair liquid flow. This channel is provided because it will be difficult for the water to reach the membrane 3 if the sleeves 21,22 are only separated by the thickness of the membrane 3 even when the holes 23 are perfectly aligned. The sleeves 21,22 can be made of any of material that will not interfere with the measurements. Stainless steel and polymers (plastics) are preferred, but material selection must be made with the application in mind, i.e. stainless steel is not acceptable when an ultrasensitive iron monitor is desired. Nickel is a good choice for sea water but copper is even better because it forms a natural biocide ($CuCO_3$) with the carbonate in sea water and this protects the system from fouling. The detection apparatus and light sources required to operate the reservoir FOCS are known in the art and are shown schematically by source/detector assembly 56, FIG. 15 which is positioned at the other end of optical fiber 6 from reservoir FOCS 20. An assembled view of FOCS 20 is shown in FIG. 2B. FIG. 2C is a sectional view along line x—x of FIG. 2B showing flow through the lateral walls 21,22 and membrane 3. The components are modular in design and can be quickly and precisely assembled, e.g. parts are threaded so they can be screwed together. For example, as shown in FIGS. 2A,B, inner cylinder 21 screws into inside threads of top cap 26 and outer cylinder 22 screws onto outer threads on caps 26; fiber optic connector 28 screws onto outer threads of adapter 27 which extends from cap 26. Other attachment means could also be used.

Figure 3A:
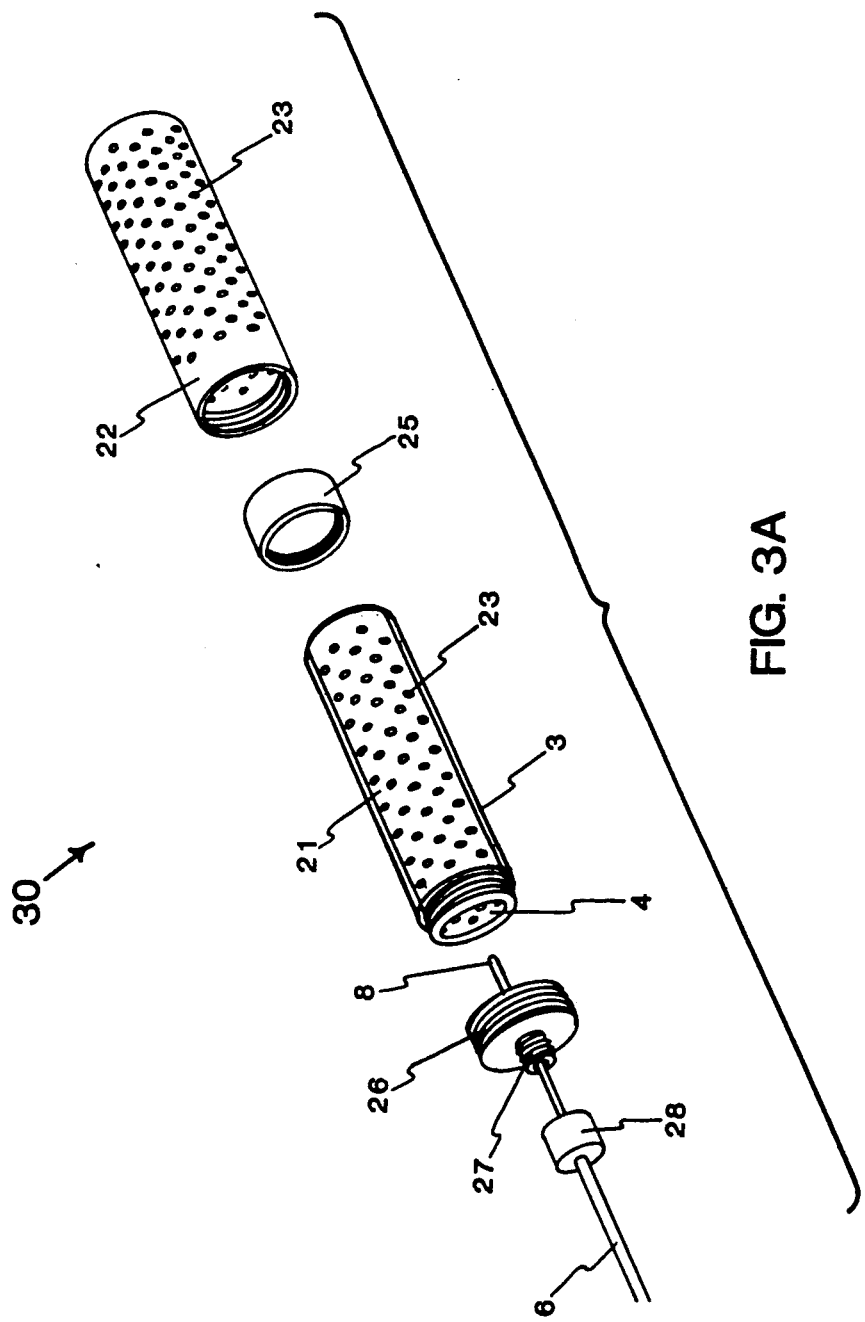
FIGS. 3A,B show exploded and assembled perspective views of a modular single fiber reservoir FOCS for the analysis of vapor and gas (atmospheric) samples.
Figure 3B:
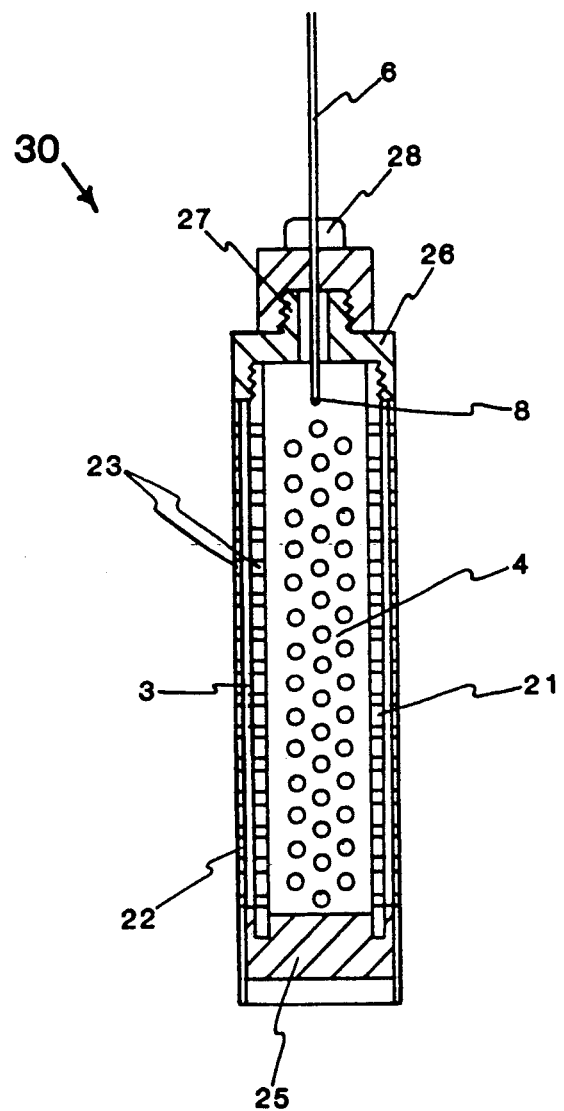

As shown in FIGS. 3A,B, a reservoir FOCS 30 is formed which is similar to reservoir FOCS 20, FIG. 1A. FOCS 30 is for atmospheric or gas analysis while FOCS 20 is for water or other liquid measurements. The differences between reservoir FOCS 20 and reservoir FOCS 30 is that spacers 29 are removed and the inner and outer sleeves 21,22 are separated by the membrane 3 only. The gas (air) flows through the holes 23 and membrane 3 and interacts with the sensing solution 4. The holes 23 in the inner and outer sleeve 21,22 are placed so that they can be aligned for maximum gas transport. Gas mobility across the membrane can be controlled by the hole 23 alignment and this affects reaction rates, and thus sensor sensitivity, operational lifetime and precision. The detection apparatus and light sources required to operate the reservoir FOCS are known in the art and are shown schematically by source/detector assembly 56, FIG. 15 which is positioned at the other end of optical fiber 6 from reservoir FOCS 30. An assembled view of FOCS 30 is shown in FIG. 3B. The remaining components are similar to those in FIGS. 2A-B.

Figure 4A:
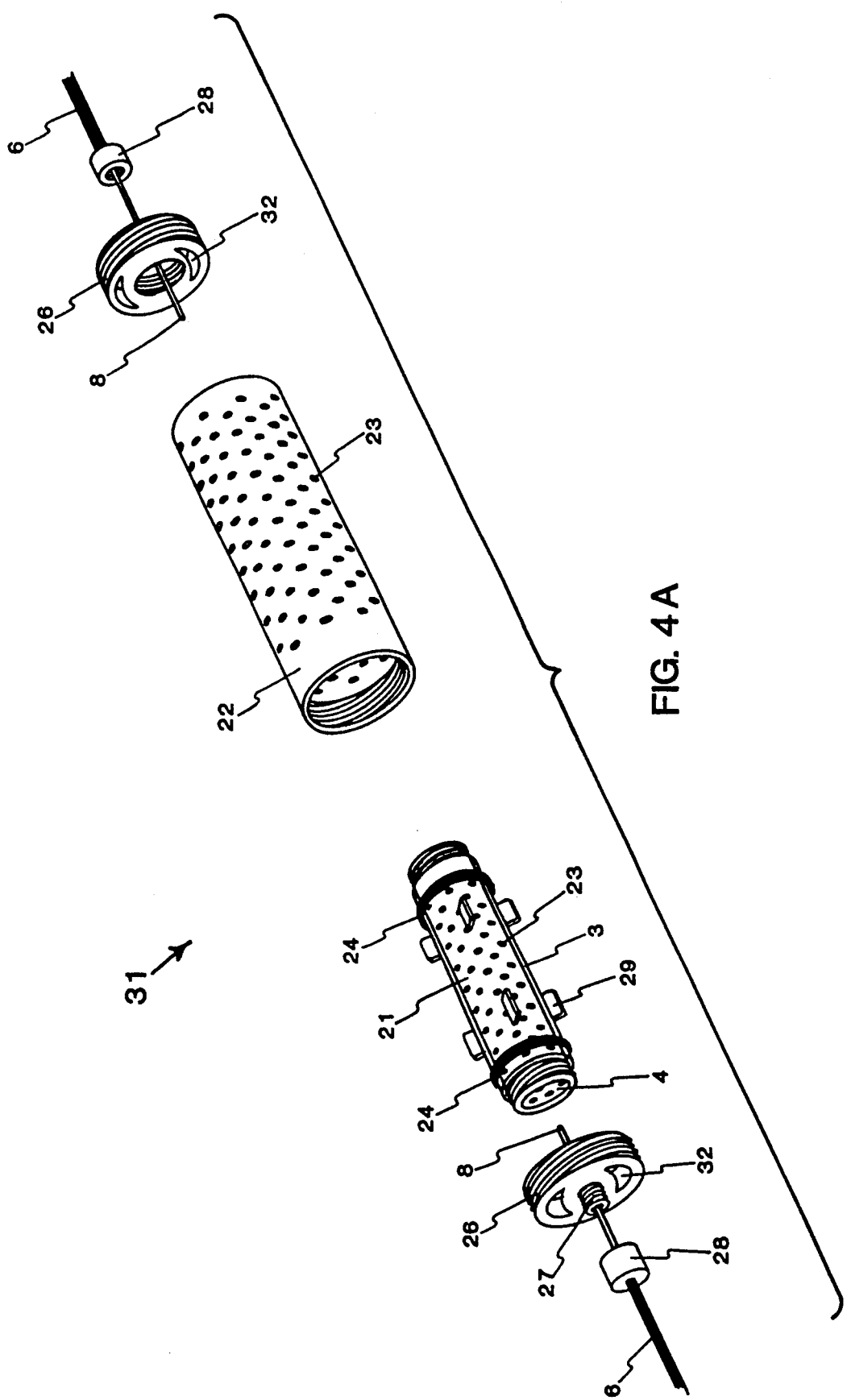
FIGS. 4A,B show exploded and expanded perspective views of a two (2) fiber embodiment of the modular reservoir FOCS shown in FIGS. 2A,B.
Figure 4B:
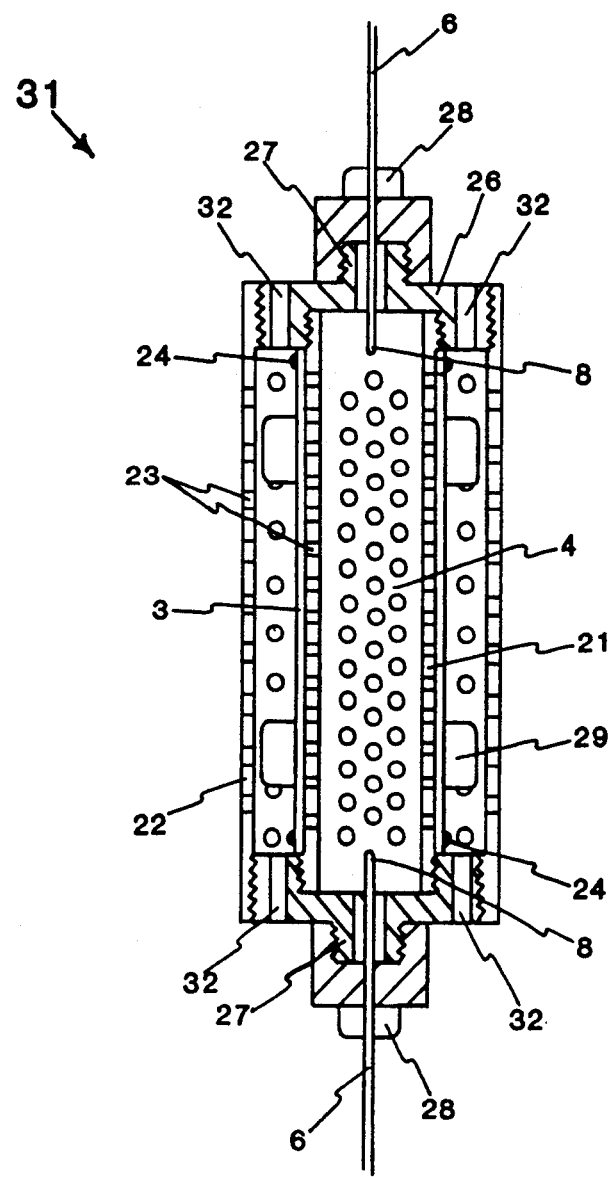

As shown in FIGS. 4 A,B a reservoir FOCS 31 can be constructed for water or other liquid analysis which uses two (2) fibers rather than FOCS 20 which uses one (1). FIG. 4A is an exploded view of reservoir FOCS 31. The design incorporates the use of an inner sleeve 21 and an outer sleeve 22. These sleeves 21,22 have large holes 23 so that water containing the species to be measured can come in contact with the membrane 3 so the species can reach the sensing reagent 4. The membrane 3 is tightly wrapped around the inner sleeve 21 and held in place with either "O" rings or plastic straps 24. Two (2) tri-purpose caps 26 are used to effect liquid tight seals at the top and bottom of sleeve 21. The caps 26 also are used as supports to which the top of the outer sleeve 22 can be attached. The channel holes 32 are outside the radius of sleeve 21 and inside the radius of sleeve 22 so that liquid can flow between the two (2) sleeves 21,22. The cap 26 contains an adapter 27 which completes the liquid tight seal when the fiber optic 6 in its connector 28 is inserted into the cell. Caps 26 also are used to seal the edges of the membrane 3 so that liquid can neither seep in nor out of the sensor. One end of sleeve 21 is closed with cap 26. The membrane 3 covered cylinder 21 with one end closed is placed upright, while making sure that fiber optic 6 is not damaged, and filled with the sensing reagent 4. The other end of sleeve 21 is then sealed with the second cap 26, adapter 27, connector 28 and fiber optic 6. The tips 8 of the fiber optics 6 are positioned in the inner sleeve 21 so that they are in the sensing solution 4 and directly aligned with each other. The relative spacing between the inner and outer cylinders 21,22 is critical because it is important to assure that transport through the membrane remains the rate limiting factor, i.e., that the rate the water reaches the membrane 3 is not retarded. This spacing is controlled by the diameter of caps 26. Spacers 29 can be used to maintain the spacing and to keep the membrane 3 taut. The liquid channel is provided because it will be difficult for the water to reach the membrane 3 if the sleeves 21,22 are only separated by the thickness of the membrane 3 even when the holes 23 are perfectly aligned. The sleeves 21,22 can be made of any of material that will not interfere with the measurements. Stainless steel and polymers (plastics) are preferred, but material selection must be made with the application in mind, i.e. stainless steel is not acceptable when an ultrasensitive iron monitor is desired. Nickel is a good choice for sea water but copper is even better because it forms a natural biocide ($CuCO_3$) with the carbonate in sea water and this protects the system from fouling. The detection apparatus and light sources required to operate the reservoir FOCS are known in the art and are shown schematically by source/detector assembly 82, FIG. 16. An assembled view of FOCS 31 is shown in FIG. 4B.

Figure 5A:
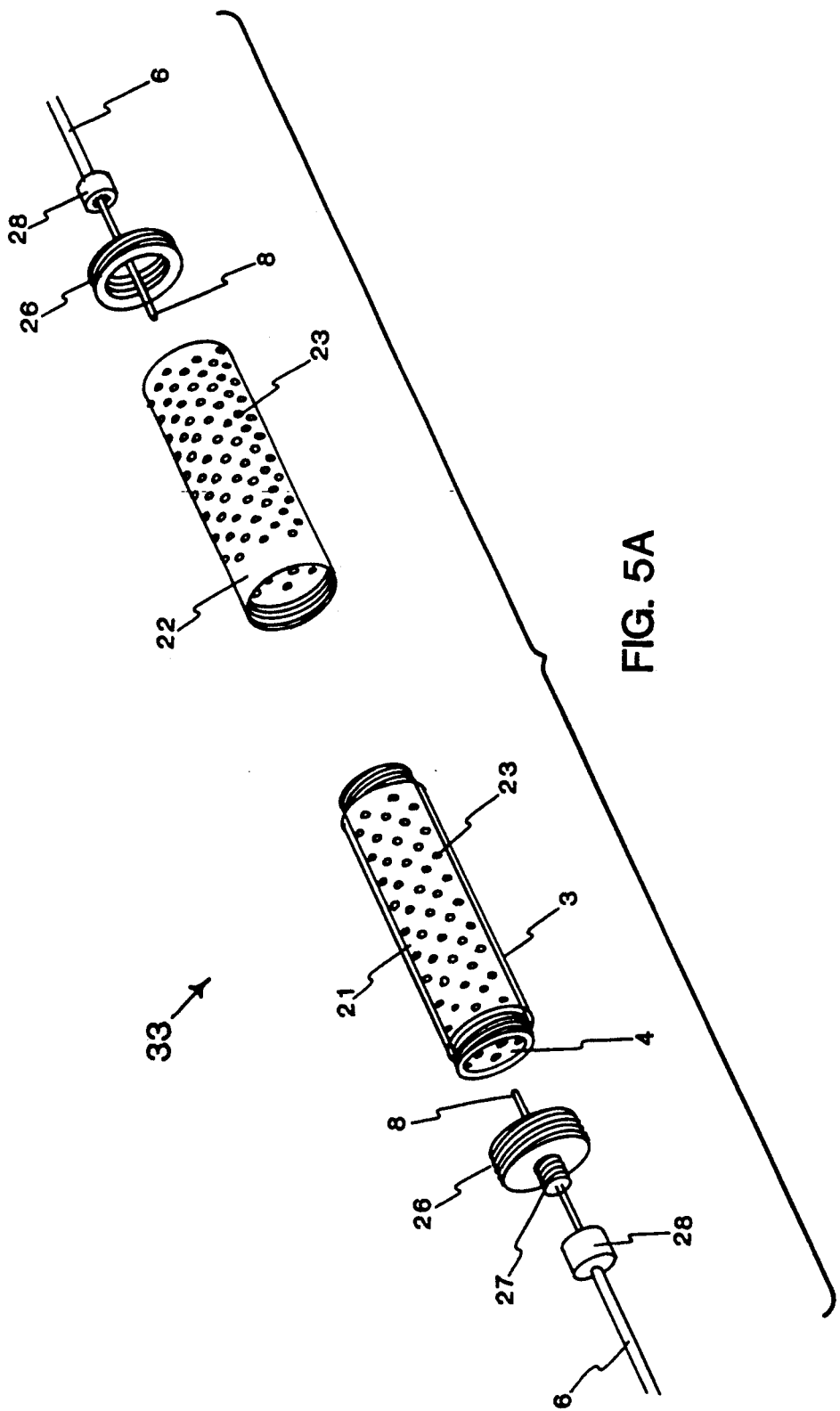
FIGS. 5A,B show exploded and assembled perspective views of a two (2) fiber embodiment of the modular reservoir FOCS shown in FIGS. 3A,B.
Figure 5B:
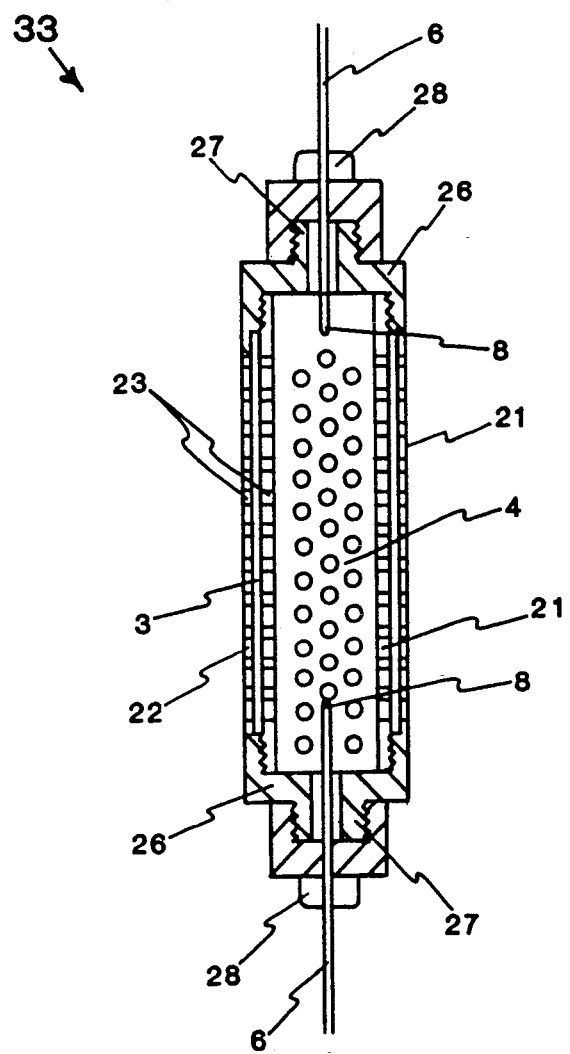

As shown in FIGS. 5A,B, a reservoir FOCS 33 is formed which is similar to FOSC 30, FIGS. 3A,B, except that FOCS 33 uses two (2) fibers instead of one (1). The differences between reservoir FOCS 33 and reservoir FOCS 31, shown in FIGS. 4A,B, is that spacers 29 are removed and the inner and outer sleeves 21,22 are separated by the membrane only. The gas (air) flows through the holes 23 and interacts with the sensing solution 4. Gas mobility across the membrane can be controlled by the hole 23 alignment. The detection apparatus and light sources required to operate the reservoir FOCS are known in the art and are shown schematically by source/detector assembly 82, FIG. 16. An assembled view of FOCS 33 is shown in FIG. 5B.

Figure 6A:
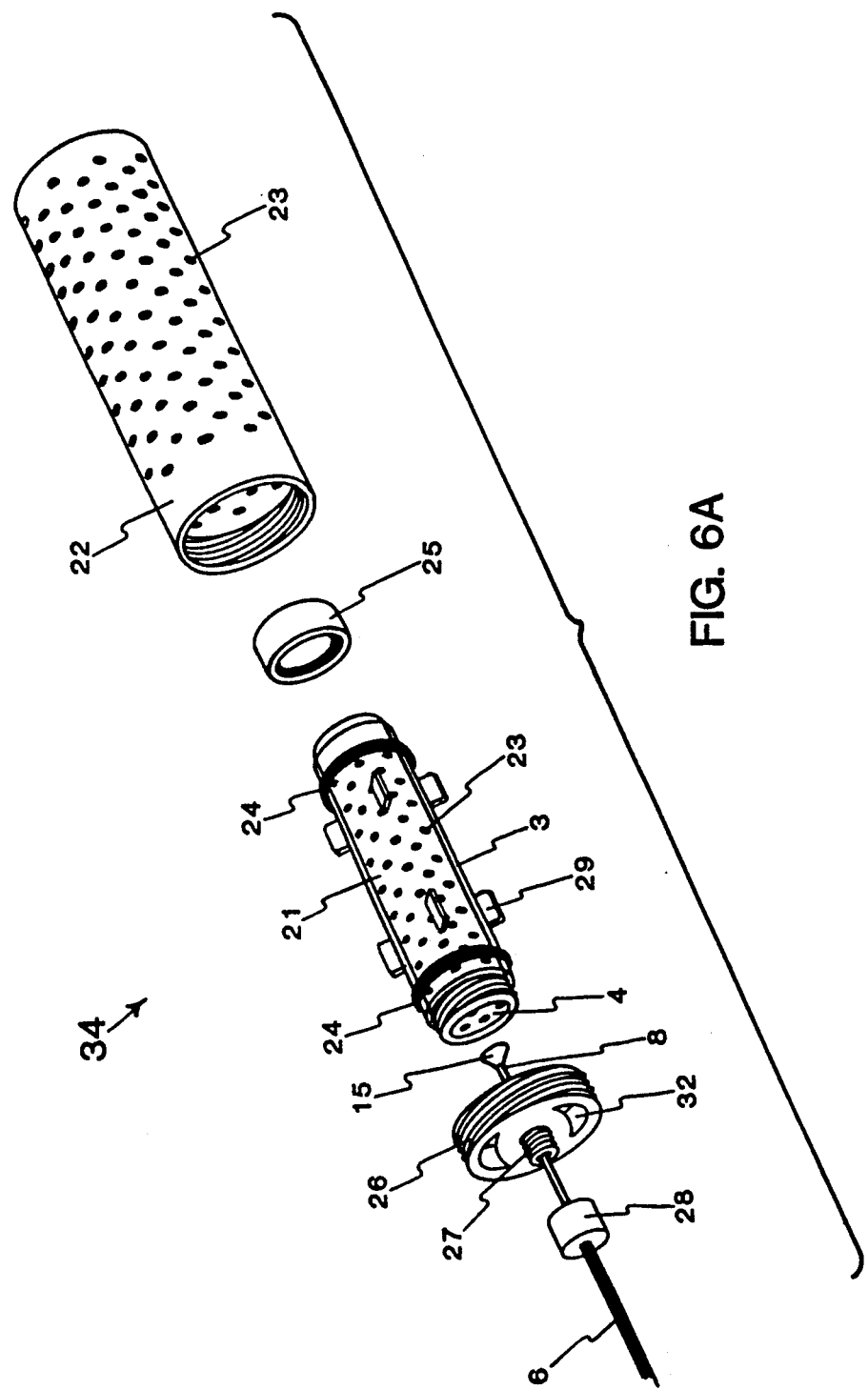
FIGS. 6A,B show the modular reservoir FOCS shown in FIGS. 2A,B and 3A,B with a lens to increase field-of-view and light collection ability.
Figure 6B:
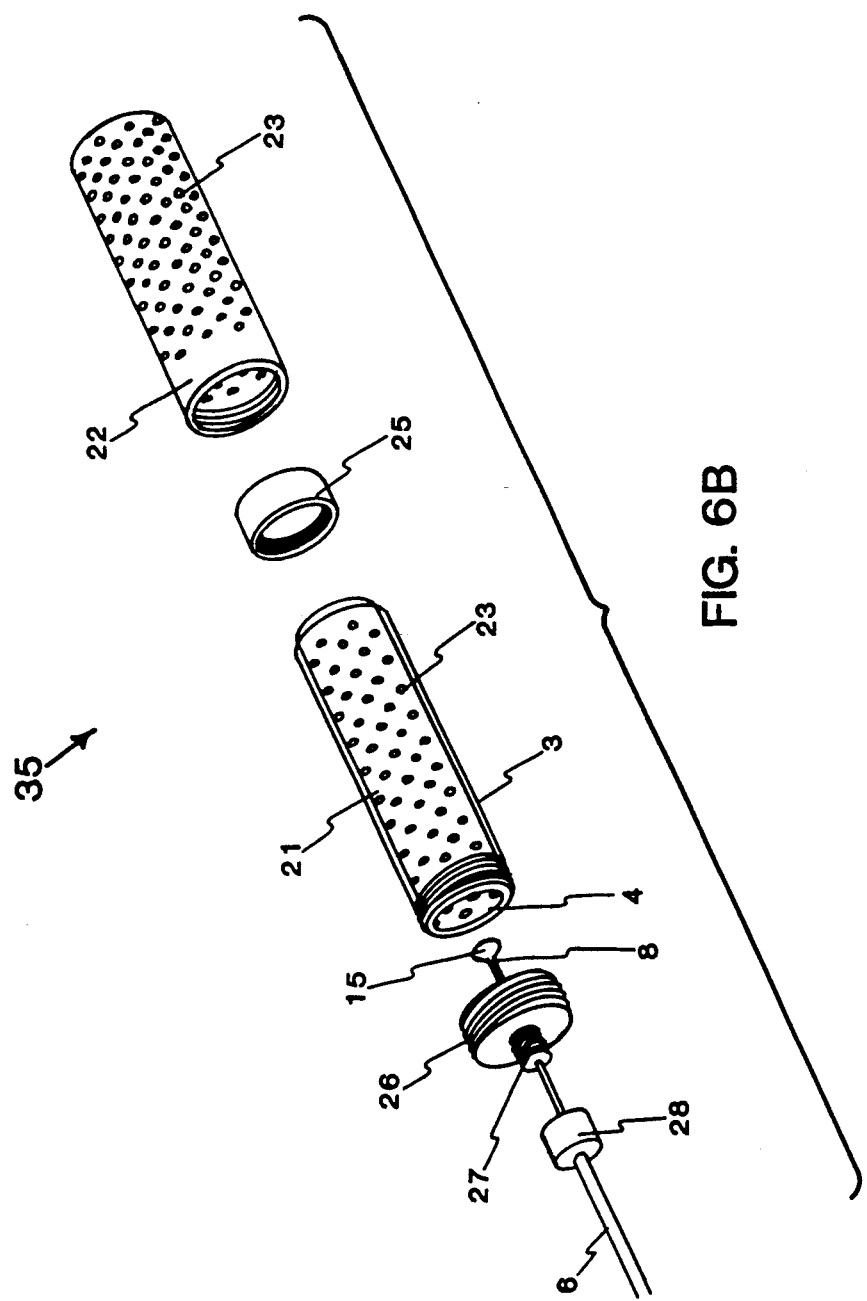

As shown in FIGS. 6A,B FOCS 34,35 are adaptations of FOCS 20, FIGS. 2A,B and FOCS 30, FIGS. 3A,B. In FOCS 34,35 a diverging lens 15 is attached to the fiber tip 8 to increase its field-of-view and light collection ability. This adaption can be used with either the gas or liquid versions of the FOCS. Lens 15 can be attached to fiber tip 8 using lens mount 16 (shown in FIG. 1D) or optical cement. Thus, an improved optical interface between a chemical sensor and a fiber optic may be utilized. The optical interface may be used with a variety of FOCS designs that utilize fluorescence, absorption, refraction and reflection techniques.

Figure 7A:
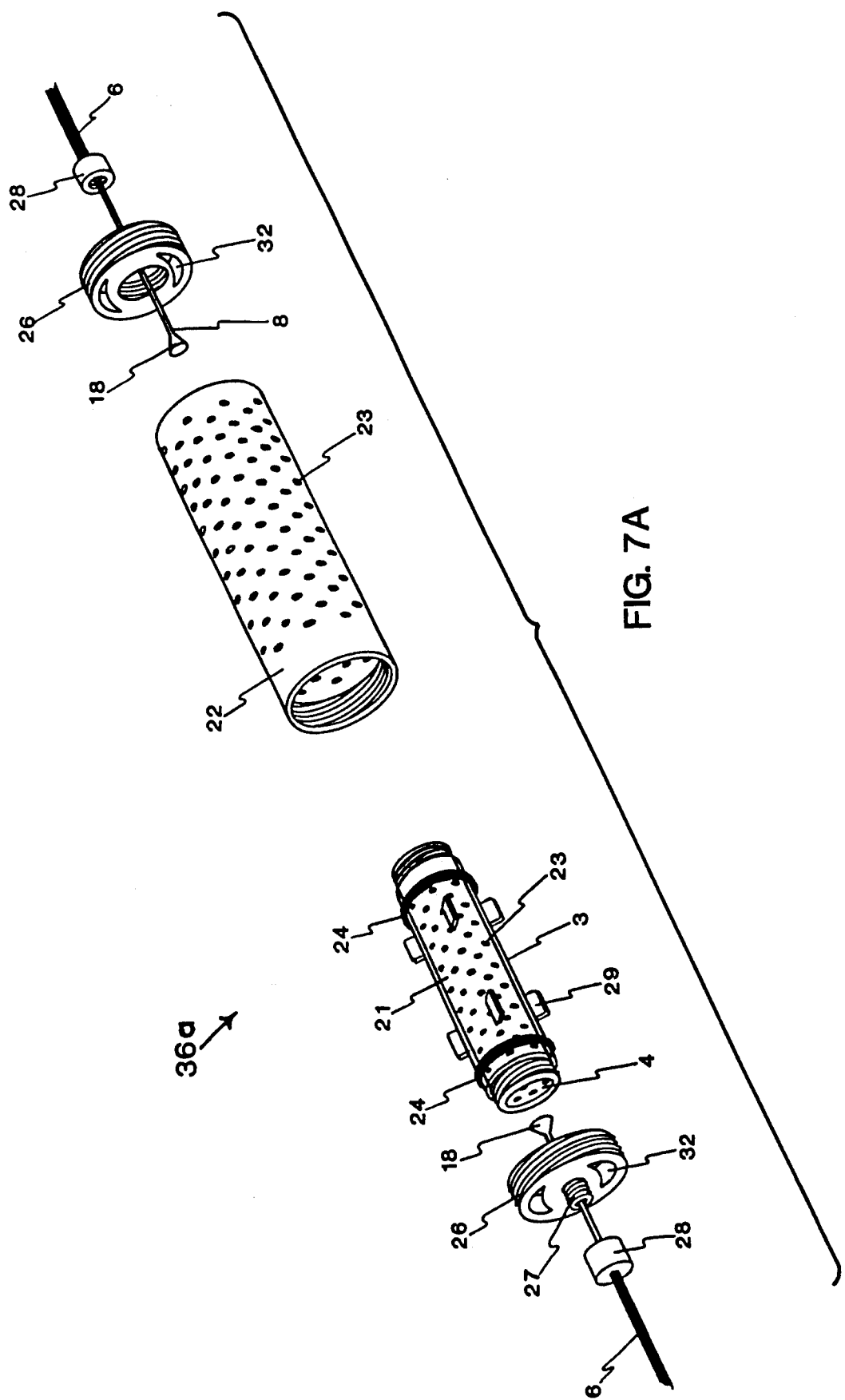
FIGS. 7A,B show the modular reservoir FOCS shown in FIGS. 4A,B and FIGS. 5A,B with collimating lenses to increase the size of the observed sample volume and to improve the efficiency of light collection.
Figure 7B:
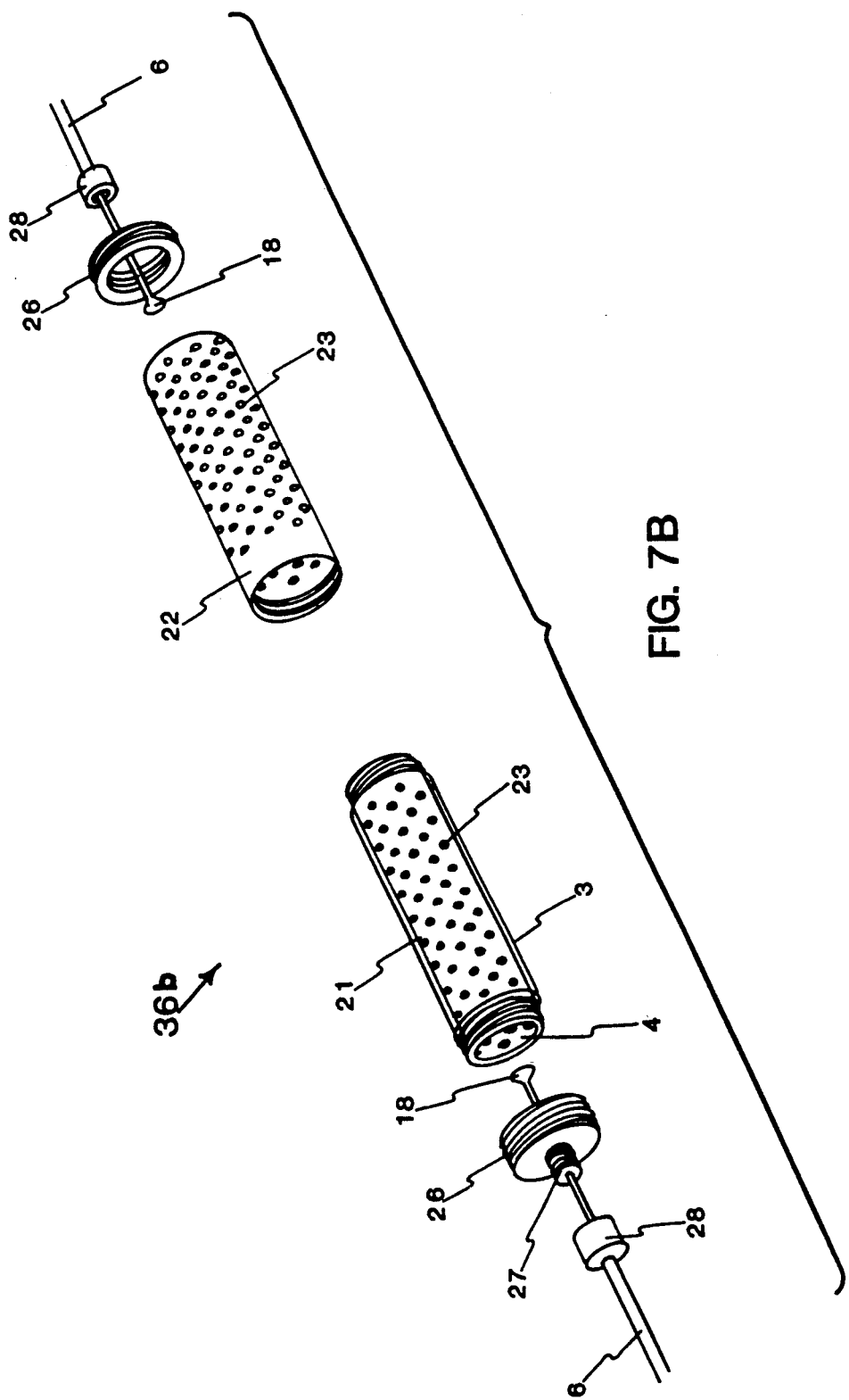

As shown in FIGS. 7A,B, FOCS 36a,b are modifications of FOCS 31, FIGS. 4A,B and FOCS 33, FIGS. 5A,B. In FOCS 36a,b two (2) collimating lenses 18 increase the size of the sample volume and optimize the use of the excitation light and improve collection of the emitted light. The collimating lenses are attached to fiber tips 8 with either a lens mount 16 (shown in FIG. 1E) or optical glue. When properly aligned the lenses form a well-defined cylinder of light which is transmitted across FOCS 36a,b. The first lens 18 takes the light coming out of the fiber optic and expands it to form a cylinder of light while the second lens 18 takes the column of light and refocuses into the second fiber. This layout may be used with a variety of FOCS designs that utilize fluorescence, absorption, refraction and reflection techniques.

Figure 8A:
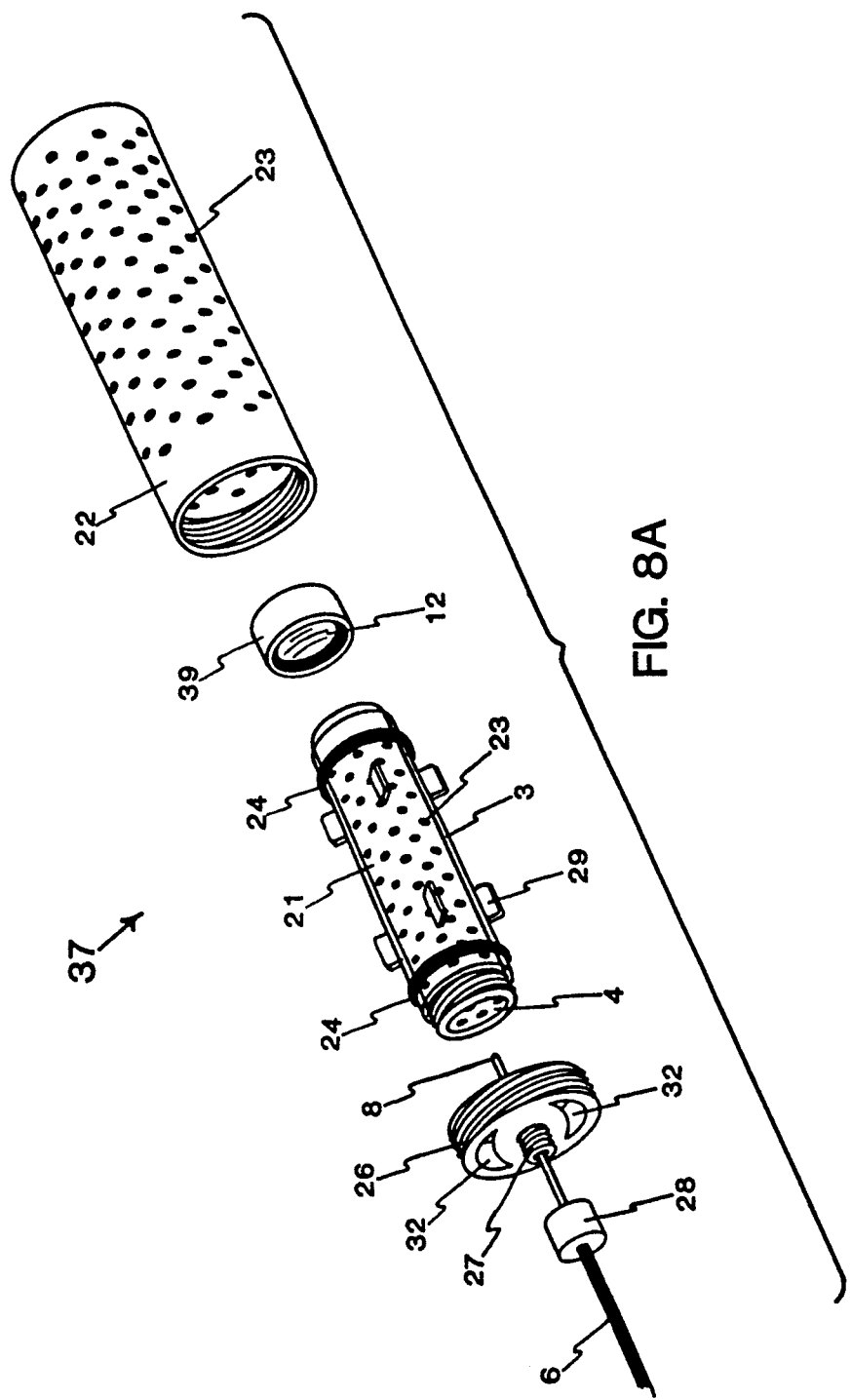
FIGS. 8A,B show the modular reservoir FOCS shown in FIGS. 2A,B and 3A,B with a focusing mirror to improve the efficiency of light collection.

As shown in FIGS. 8A,B FOCS 37,38 are adaptations of FOCS 20, FIGS. 2A,B and FOCS 30, FIGS. 3A,B. In FOCS 37,38 a focusing mirror 12 is attached to a modified end cap 25 to form a focusing cap 39. Cap 39 not only seals the bottom of sleeve 21, but is adjustable so that the focal point of the mirror is at fiber tip 8. The use of focusing mirror 12 increases the amount of emitted light that reaches fiber tip 8. This adaption can be used with either the gas or liquid versions of the FOCS. This optical interface may be used with a variety of FOCS designs that utilize fluorescence, absorption, refraction and reflection techniques.

Figure 9A:
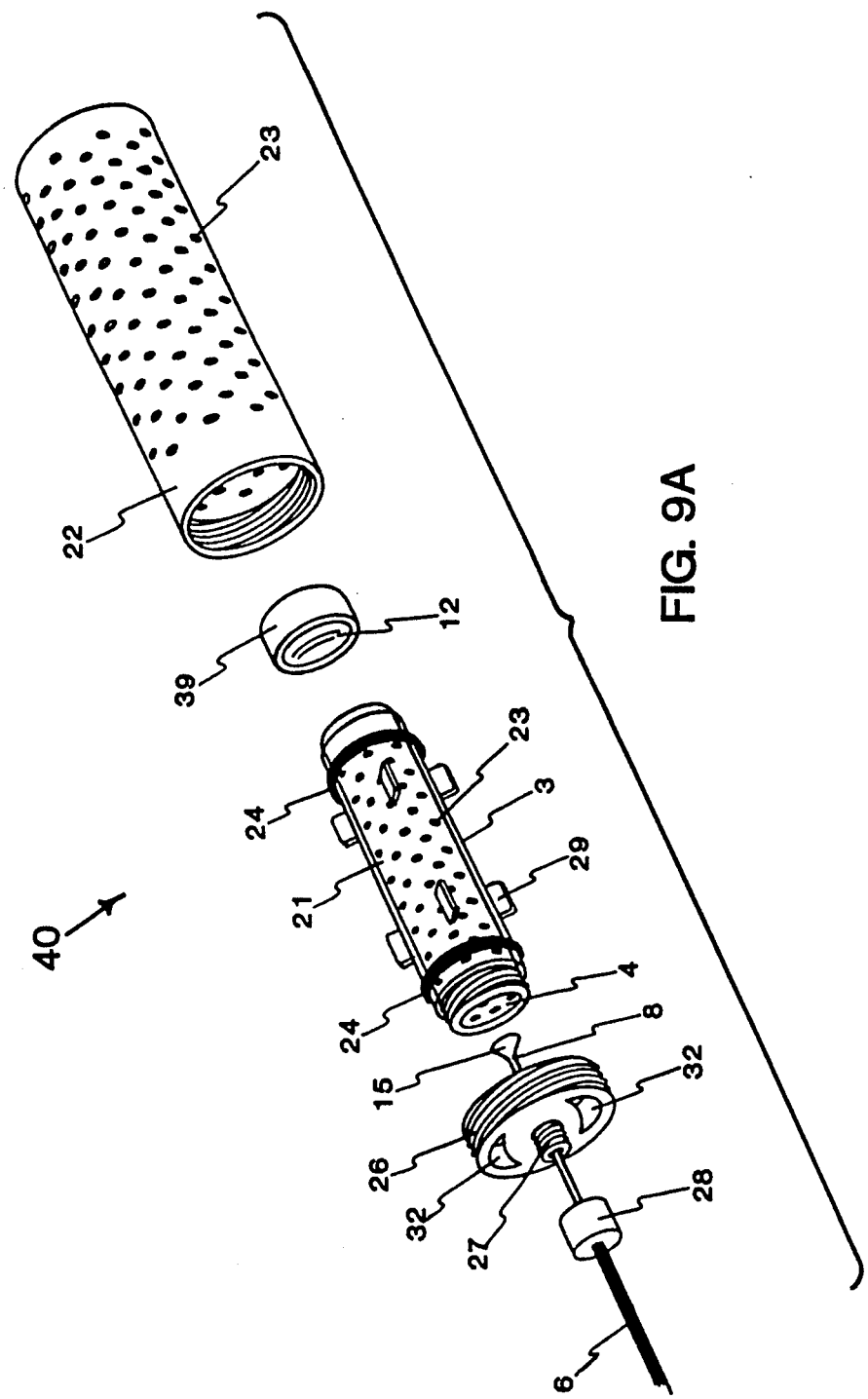
FIGS. 9A,B show the modular reservoir FOCS shown in FIGS. 2A,B and 3, A,B with a lens and focusing mirror to increase the size of the observed sample volume and to improve the efficiency of light collection.

As shown in FIGS. 9A,B FOCS 40,41 are adaptations of FOCS 34,35 FIGS. 6A,B and FOCS 37,38 FIGS. 8A,B. In FOCS 40,41 both a diverging lens 15 and a focusing mirror 12 are used. Lens 15 can be attached to fiber tip 8 using lens mount 16 (as shown in FIG. 1F) or optical cement. The focusing mirror is attached to cap 39. The diverging lens 15 expands the beam of light coming out of the fiber so that it fills mirror 12. Mirror 12 focuses the emitted light back onto lens 15 which focuses it into fiber tip 8. The use of diverging lens 15 expands the size of the irradiated sample volume and focusing mirror 12 increases the amount of emitted light that reaches fiber tip 8. This FOCS configuration optimizes the optical arrangement in the single fiber optic FOCS. This adaption can be used with either the gas or liquid versions of the FOCS. This optical interface may be used with a variety of FOCS designs that utilize fluorescence, absorption, refraction and reflection techniques.

Figure 10A:
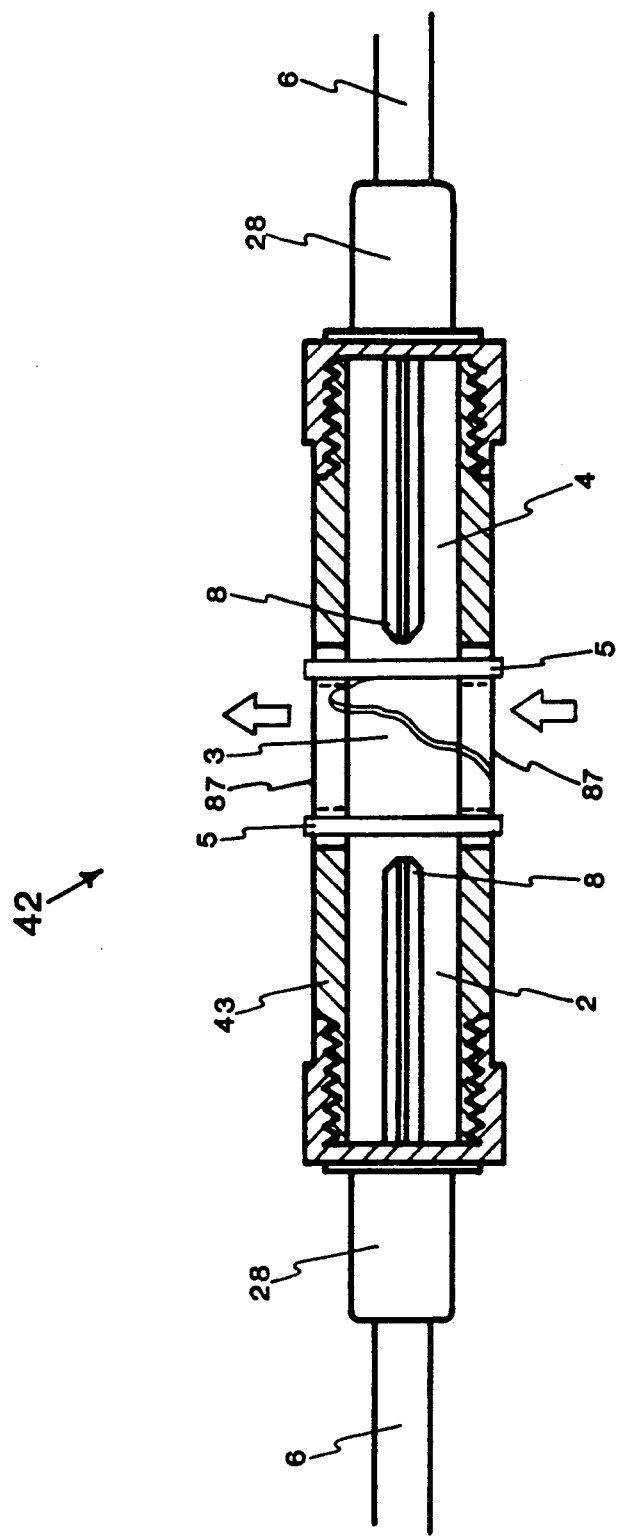
FIGS. 10A,B show sectional views of a modular reservoir FOCS, made from fiber optic connectors and a splice tube, for analysis of liquids, vapor or gases.
Figure 10B:
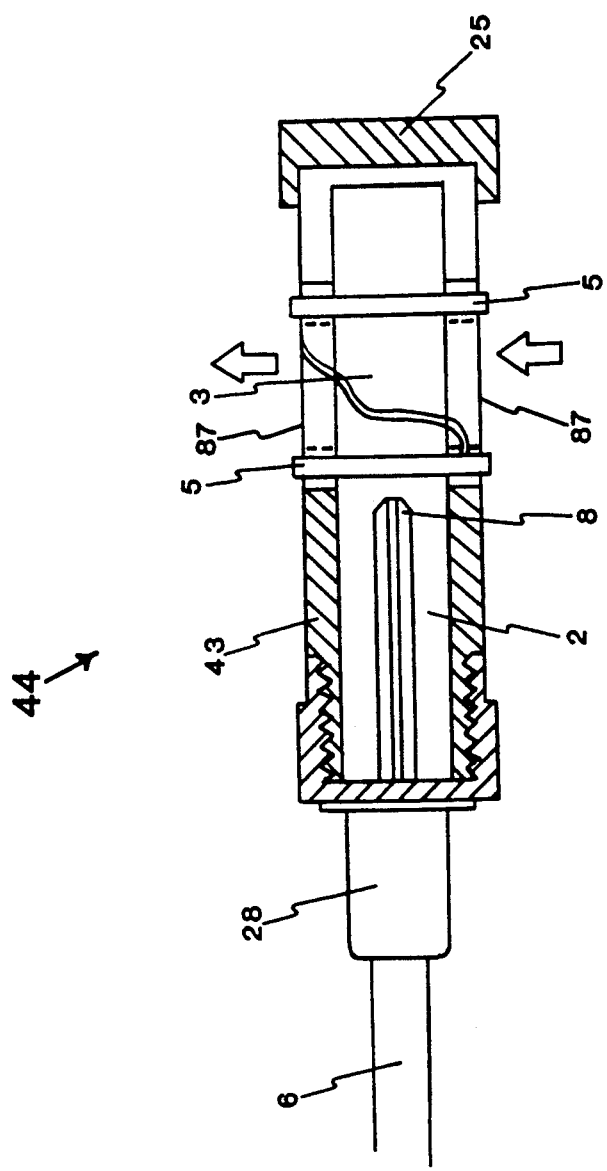

FIG. 10A shows a sectional view of modular two (2) fiber reservoir FOCS 42 for the analysis of liquids, vapors or gases made from two (2) fiber optic connectors 28 and a splice tube 43. The splice tube 43 is a hollow pipe or tube having a channel 2 therethrough and threaded to match the fiber optic connector 28. Splice tube 43 could alternately be other than cylindrical in shape and use other attachment means than threads. Opposed transverse inlet/outlet ports 87 are formed in the lateral surface of splice tube 43 so that liquids and gases can pass through the tube perpendicular to its ends. The ports 87 are covered with membrane 3 which is held tight by retaining rings 5. Each fiber optic 6 is put into a fiber optic connector 28, polished, and sealed with epoxy to make a water tight seal. One of the water tight connectors 28 with fiber optic 6 is screwed onto or otherwise attached to one end of splice 43 and the splice tube is filled with sensing reagent 4. Another water tight connector 28 with fiber optic 6 is used to seal the other end of the splice tube. It is important that the fiber optic tips 8 be aligned directly opposite each other because the sample volume and light collection are defined by the numerical aperture and alignment of fiber optics 6. The space between the fiber optic tips 8 is determined by the length of the splice. Splice tube 43, connectors 28 and fiber optics 6 can be made out of any material that is compatible with the sensing solution 4 and the species to be measured. The detection apparatus and light sources required to operate the reservoir FOCS are known in the art and are shown schematically by source/detector assembly 82, FIG. 16. In FIG. 10B, FOCS 44 shows a design similar to FOCS 42 with a single fiber. In this configuration one end of splice tube 43 is sealed with cap 25 and filled with sensing solution 4. The other end of splice tube 43 is then sealed with water tight connector 28 with fiber optic 6. A pair of opposed lateral ports 87, covered by membrane 3, allow a transverse flow across the tube. The source/detector assembly 56, FIG. 15 is used FOCS 44.

Figure 11B:
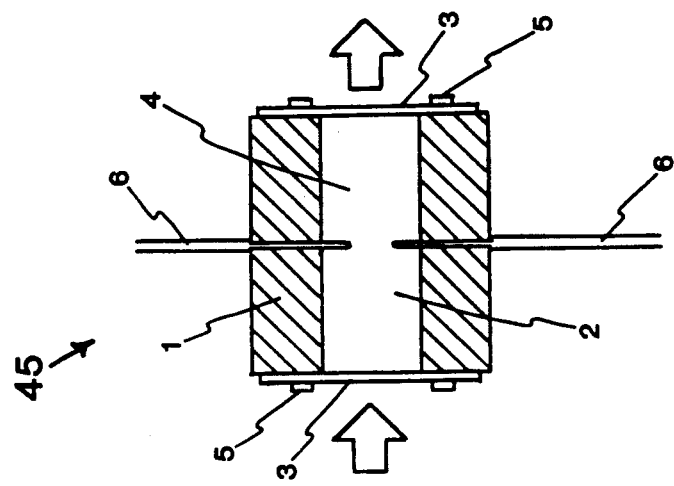
FIGS. 11A,B,C show typical views of a modular noncylindrical reservoir FOCS for analysis of liquids, vapor or gases.
FIG. 11C is a sectional view of a single fiber optic system.
Figure 11A:
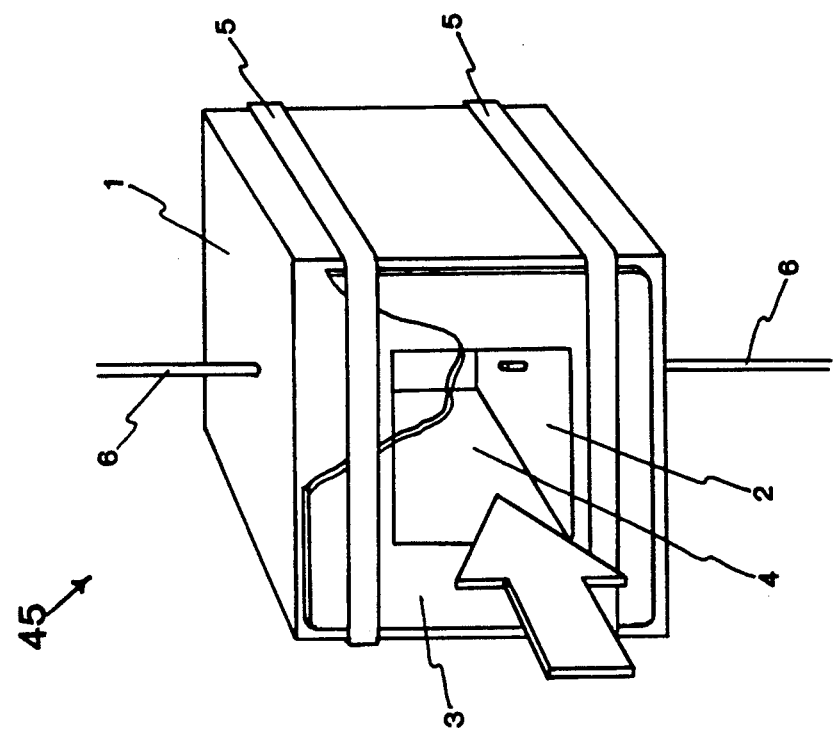
Figure 11C:
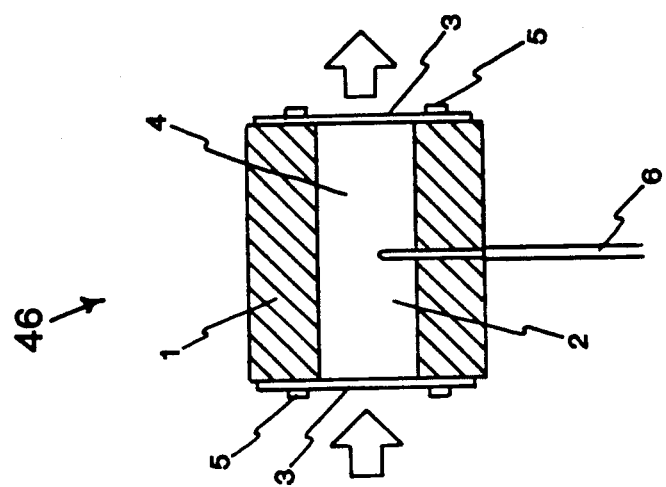
Figure 12A:
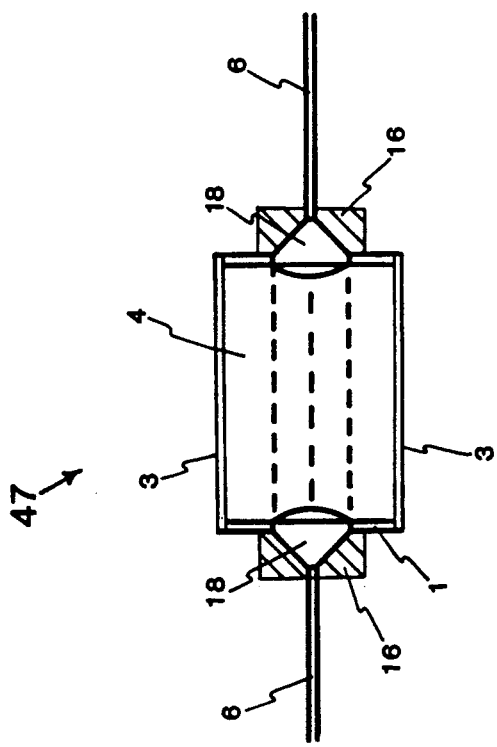
FIGS. 12A,B show a typical view of a modular reservoir FOCS with collimating lenses for the analysis of liquids, vapors or gases.

FIGS. 11 A, B show two (2) views of rectangular shaped, cross-flow FOCS 45. This is a basic design for the analysis of liquids, vapors and gases. It consists of a cell body 1 having a channel 2 extending therethrough between two opposed lateral sides of cell body 1. The open ends of channel 2 form inlet/outlet ports 87 in the opposed lateral sides of cell body 1 which are covered by membranes 3 which are held in place by retaining rings 5. The sensing solution 4 is contained in channel 2 by membranes 3. Fiber optics 6 are placed into the sides (top and bottom or ends) of the cell body 1 so that they are aligned opposite each other. Membrane 3 holds sensing reagent 4 in FOCS 45 while allowing the species to be analyzed to enter channel 2 and interact with sensing reagent 4. The electronics and optics are described in source/detector assembly 82, FIG. 16. Cell body 1 can be made in any shape, size and material that is compatible with the measurement scenario. The shape and size of channel 2 is also dictated by the measurements to be made. In any configuration, the channel for fluid flow through the FOCS cell is substantially perpendicular to the optical fibers. Selection of membrane material is dependent upon the sensing reagent, the species to be measured and potential interferences. FIG. 11C shows FOCS 46, a single fiber version of FOCS 45. One fiber optic 6 is placed in the side of the cell body. Source/detector assembly 56, FIG. 15 is used with FIG. 12A shows a cross-section of FOCS 47. FOCS 47 is a modular two (2) fiber sensor for the analysis of liquids, vapors and gases. The design of FOCS 47 can be applied to FOCS 42, FIG. 10A and FOCS 45, FIGS. 11A, B. FOCS 47 uses collimating lenses 18 at fiber tips 8. Lens 18 can either be attached to the end 8 of the fiber 6 with lens mount 16 (as previously shown) or optical glue. It is also possible to mount lenses 18 in the walls of cell 1 for rigidity, as shown, using lens mounts 16, if necessary. The fiber and lens can also extend into the cell as previously shown. Fiber optic 6 or lens 18 must make a water tight seal with cell body 1.

Figure 12B:
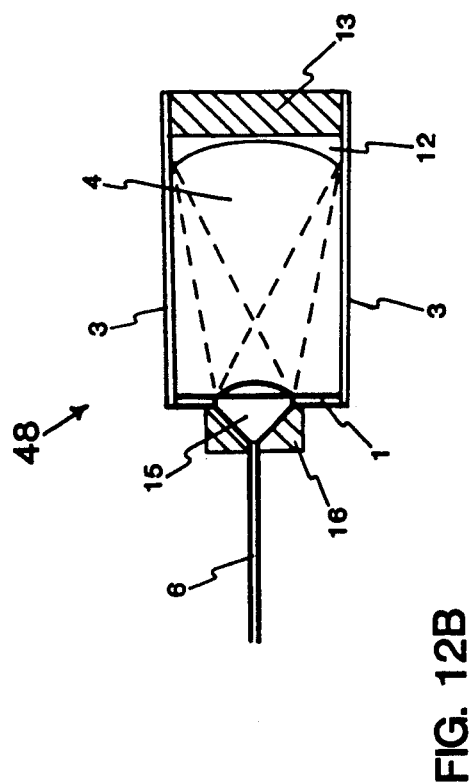

Membrane 3 on the side of cell 1 holds sensing solution 4 in channel 2. The lateral sides of cell 1 are porous or have ports formed therein to permit flow across the cell. The sample volume and light collection efficiency is described by the characteristics of the lenses 18 and their alignment. FOCS 47 is used with source/detector assembly 82, FIG. 16. FOCS 48, FIG. 12B is FOCS 47 modified for single fiber optic operation. FOCS 48 uses a diverging lens 15 and a focusing mirror 12. Lens 15 can be attached to fiber optic 6 by lens mount 16 or optical glue. Mirror 12 is attached to focusing plate 13. Fiber optic 6 with lens 15 is placed in one wall of cell body 1 and mirror 12 in plate 13 is placed in channel 2 on the wall of cell body 1 opposite fiber optic 6. The sample volume and light collection efficiency are determined by the size and optical characteristics of lens 15 and mirror 12. FOCS 48 is used with source/detector assembly 56, FIG. 15.

Figure 13:
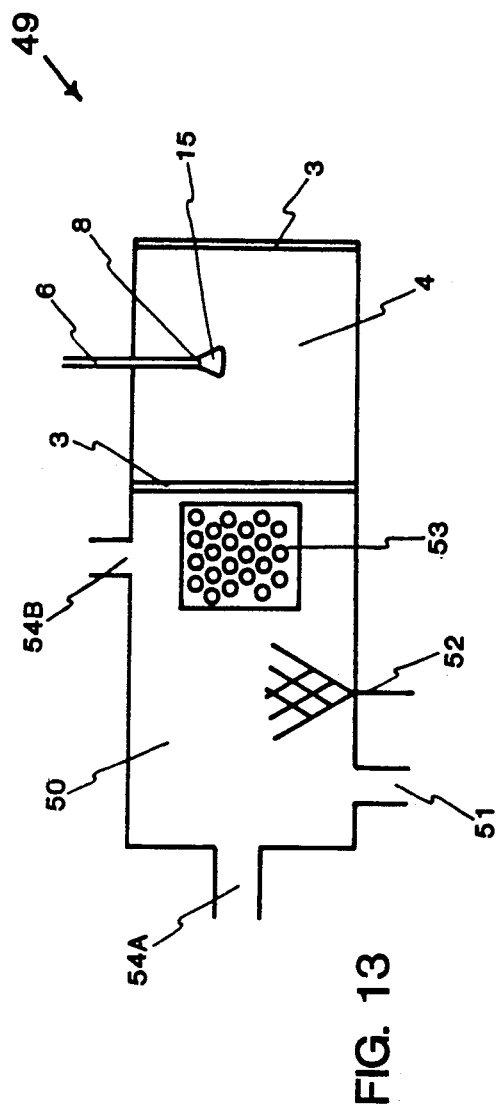
FIG. 13 shows a view of a single fiber optic reservoir FOCS with a sample preparation chamber attached.

FIG. 13 shows how single fiber optic reservoir FOCS 49 can be used with sample preparation chamber 50. Chamber 50 can be of any reasonable length. It can be used for liquids, vapors and gases. The reservoir FOCS 49 and chamber 50 share a common interface at membrane 3. Membrane 3 keeps sensing solution 4 in the reservoir FOCS while permitting the products of interest from chamber 50 to interact with sensing solution 4. This reservoir cell has the single fiber arrangement of FOCS 9. The use of fiber optic 6 with tip 8 attached to diverging lens 15, similar to FOCS 14, is more appropriate for this application. A second membrane 3a on an opposed face of FOCS 49 from membrane 3 allows a cross flow through FOCS 49. Fiber 6 is orthogonal to this direction. If there is no need for flow out of FOCS 49, membrane 3a can be eliminated and replaced by a solid wall. Chamber 50 is designed to handle most chemical reactions. The sample enters through sample inlet port 54a. Inlet tube 51 admits gases or liquids which can react with the sample. Irradiation port 52 provides an opening through which the sample can be irradiated. This includes ultraviolet, visible, infrared, microwave and nuclear excitation. Chemical bed 53 in chamber 50 provides a mechanism for liquid-solid and gas-solid reactions to occur with the sample prior to analysis. The species of interest pass through the membrane into the FOCS while the by-products are vented through outlet tube 54b. The efficiency of sample preparation can be controlled by the type of chemical reaction chosen, the length of chamber 50, and the flow rate of the sample through 50. Source/detector assembly 56, FIG. 15 is used with this system.

Figure 14:
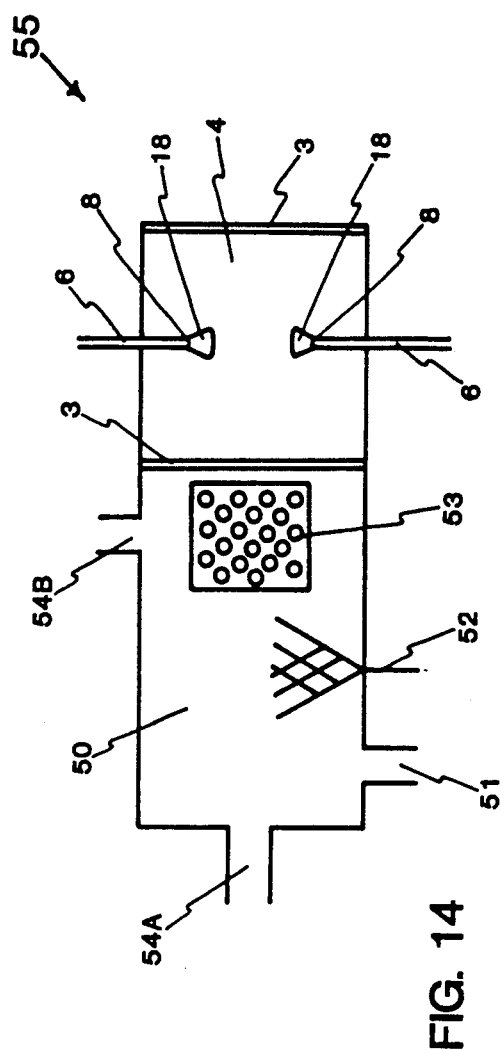
FIG. 14 shows a view of a two (2) fiber reservoir FOCS with a sample preparation chamber attached.

FIG. 14 shows how a two (2) fiber optic reservoir FOCS 55 can be used with sample preparation chamber 50. Sample chamber 50 is the same as described in FIG. 13. In this configuration two fiber optics 6 are used in the reservoir FOCS. These face each other as shown in FOCS 10. The use of collimating lenses 18 is as shown in FOCS 17. Source/detector assembly 82, FIG. 16 is used with this FOCS set-up.

Figure 15A:
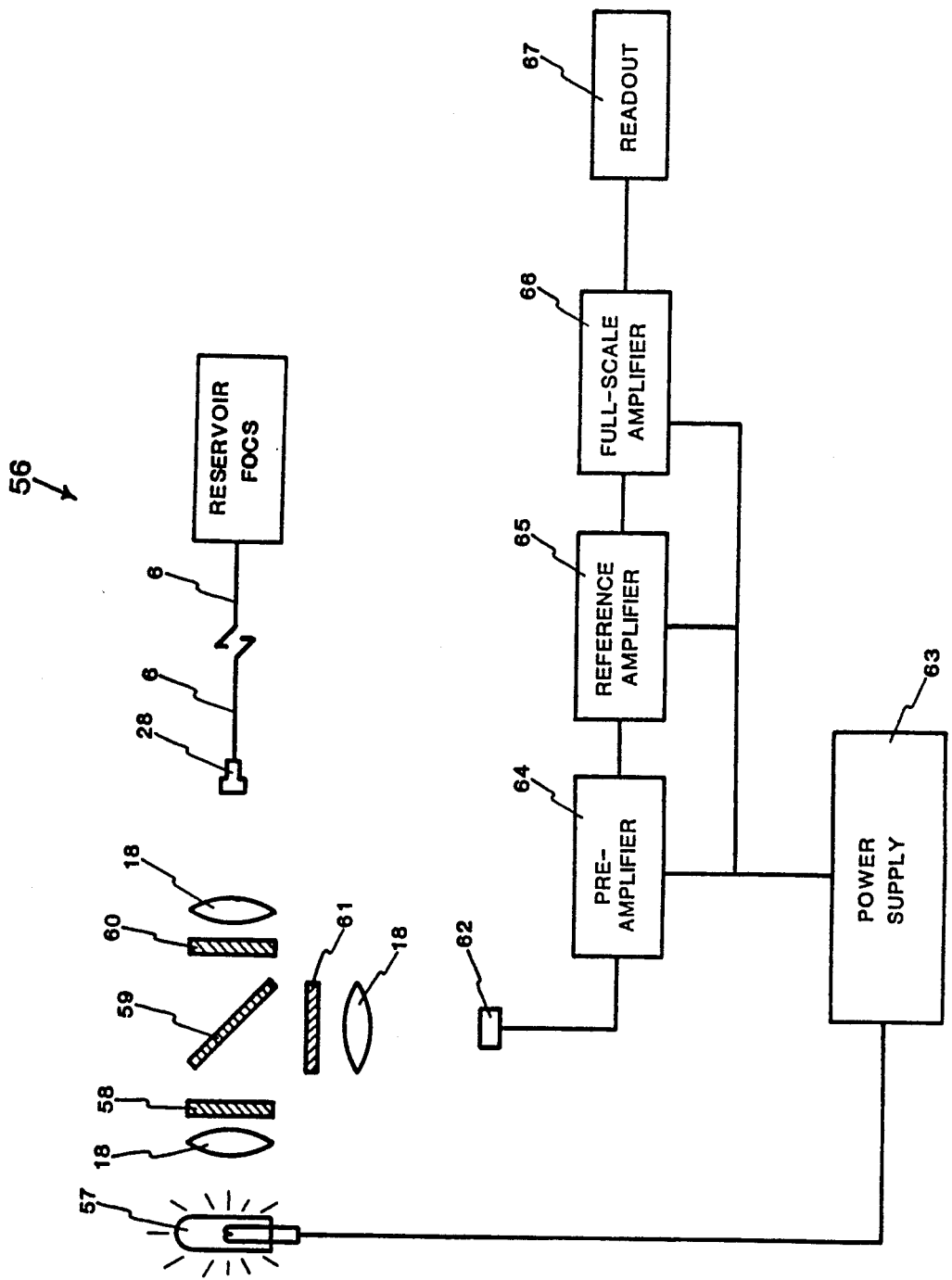
FIGS. 15A,B show the source/detector assembly for the single fiber optic reservoir FOCS.
Figure 15B:
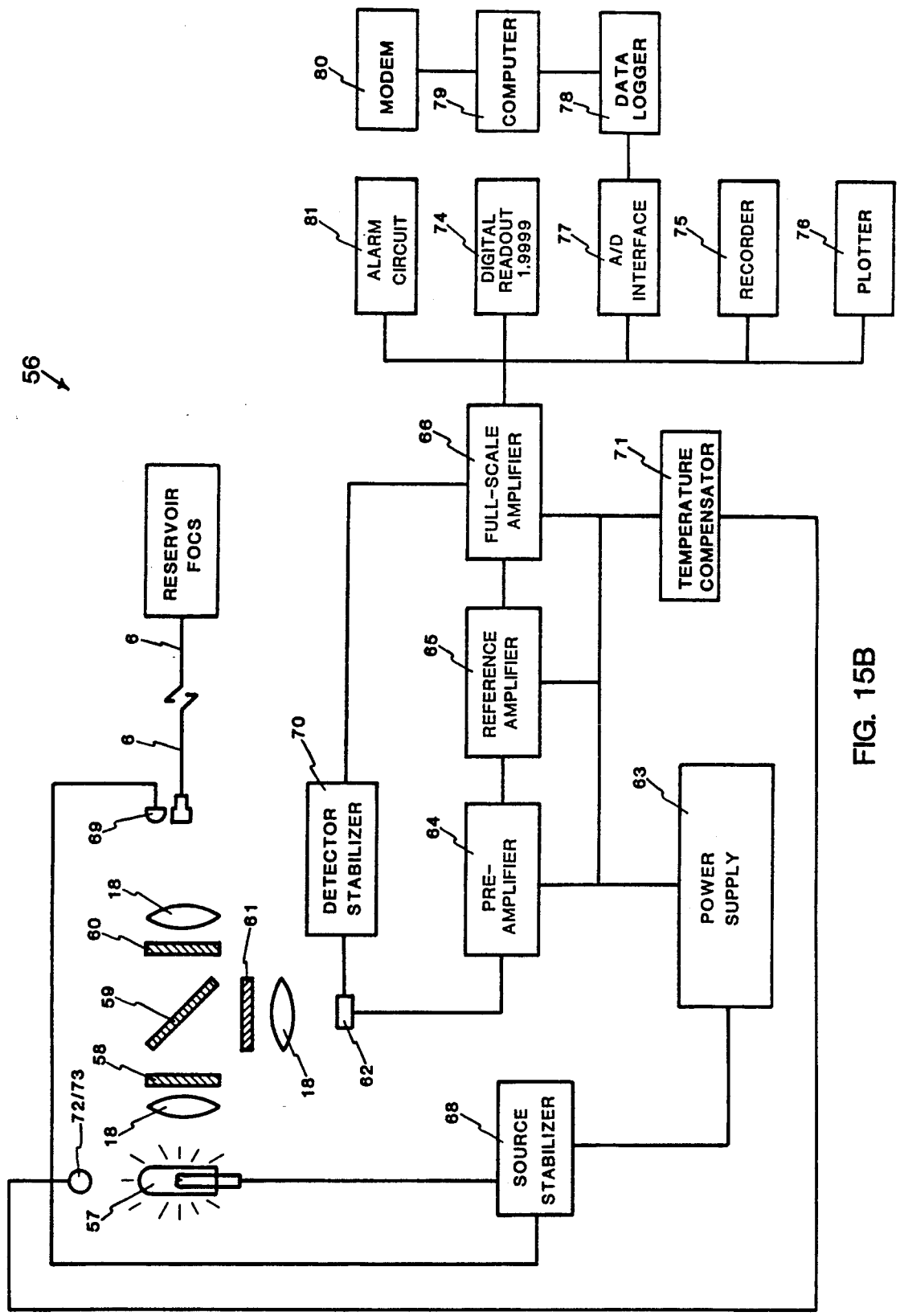

FIG. 15A shows source/detector assembly 56 which is used in conjunction with the single fiber optic reservoir FOCS. Light source 57 can be a laser, lamp or diode. The light passes through collimating lens 18 where the light beam is made parallel and then passes through one or more source color filters 58 at 90° to the filters' face. Filters 58 are used to make the source 57 light monochromatic. Several filters may be needed to accomplish this task when very narrow wavelength bands are required. Color filters 58, 60, 61, in the optical train, will have different wavelengths and band passes depending on what color (wavelength) light is to be transmitted and detected. Color filters 58, 60, 61 can be replaced by any type of spectral sorter. In fluorescence the excitation and return wavelengths are different whereas in absorption they are the same. Normally when light source 57 is a laser or diode, filters 58 can be eliminated. The parallel light goes through dichroic mirror 59 which is placed at 45° to the light beam. The angle between the light beam and the dichroic mirror can vary depending on the optical coating on the dichroic mirror and the wavelength of light to be transmitted. In select arrangements dichroic mirror 59 can be replaced with a beam splitter. The parallel light passing through dichroic mirror 59 goes through one or more additional color filters 60 and to a second collimating lens 18 which brings the light to focus on the optical fiber 6 in connector 28. The light propagates along fiber optic 6 to its tip 8 which is in a reservoir FOCS. The data-containing signal from the FOCS returns up the same fiber and exits out of the connector through collimating lens 18 where it is made parallel and passes through filters 60 at 90°. The light then strikes beam splitter 59 and is reflected into additional color filter(s) 61 through another collimating lens 18 which brings it to focus on detector 62. Detector 62 converts the light intensity into an electrical signal for processing. Detector 62 is selected to have optimum response to the wavelength of the return light. The electronics needed to operate the reservoir FOCS system consist of power supply 63, pre-amplifier 64, reference amplifier 65, full scale amplifier 66 and readout 67. Options which improve the stability and data collection ability of the system are shown in FIG. 15B. These may be used individually or collectively. Source 57 is stabilized by measuring its intensity and automatically correcting for variations. Source intensity can be monitored at any point in the optical train. Placing source detector 69 at the input connector 28 to fiber optic 6 has been shown to be best. The signal from detector 69 is fed to source stabilizer 68 which controls the input power to source 57 through power supply 63. Detector 62 is steadied by detector stabilizer 70 which feeds-back to amplifier 66. Amplifier 66 then adjusts the sensitivity of detector 62. To assure that there are no adverse temperature effects, temperature compensator 71 is used in connection with a temperature sensor. For most situations thermistor 72 is used as the temperature transducer (sensor). When higher sensitivity or precision is required, thermistor 72 is replaced with the more temperature sensitive piezoelectric crystal 73. Readout 67 can be digital display 74 or a variety of recorders 75 or plotters 76. Automated systems include A/D interface 77, data logger 78, computer 79 and plotter 76 and the appropriate software. Data can be obtained from remote FOCS sites using modem 80 or a telemetering hook-up. Alarms 81 for instrument failure, changing trends and emergencies are also provided.

Figure 16A:
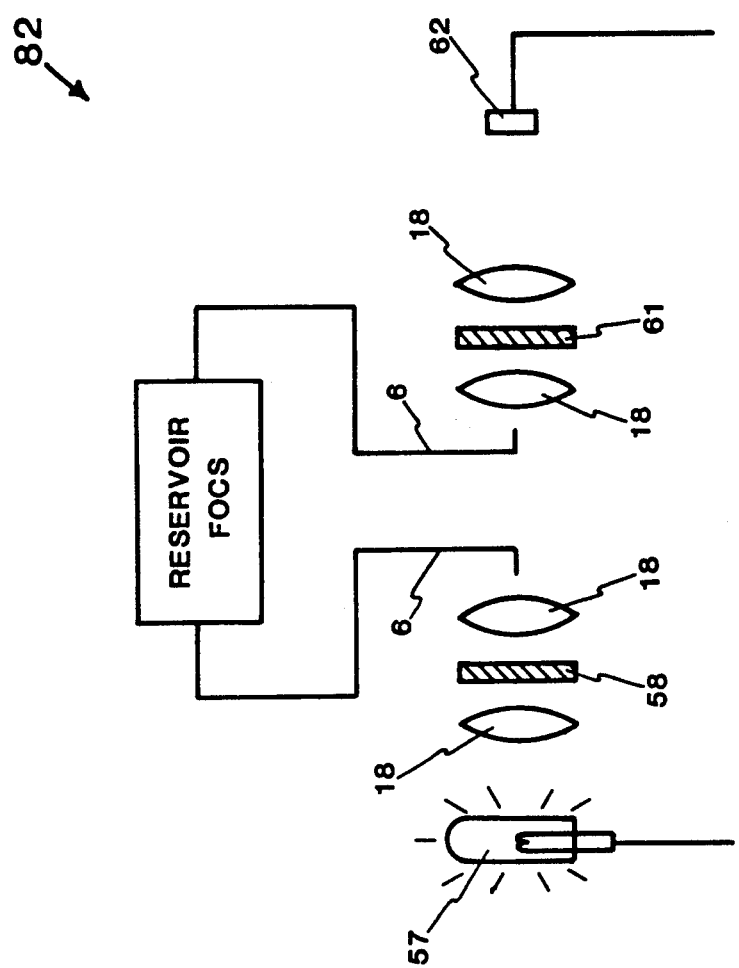
FIGS. 16A,B show the source/detector assembly for the two (2) fiber optic reservoir FOCS.
Figure 16B:
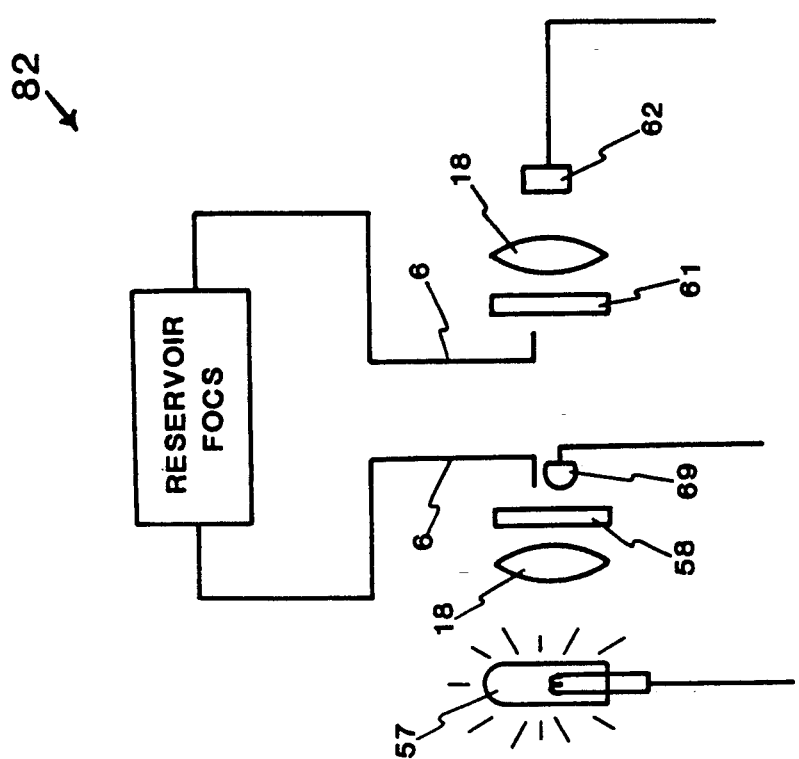

FIG. 16A shows source/detector assembly 82 which is used in conjunction with the two (2) fiber optic reservoir FOCS. In this configuration the reservoir FOCS becomes an integral part of the optical train. In this application dichroic mirror 59 and filters 60 are not used. Light source 57 can be a laser, lamp or diode. The light passes through collimating lens 18 where the light beam is made parallel and then passes through one or more source color filters 58 at 90° to the filters' face. Filters 58 are used to make the source 57 light monochromatic. Several filters may be needed to accomplish this task when very narrow wavelength bands are required. Color filters 58, 61, in the optical train, will have different wavelengths and band passes depending on what color (wavelength) light is to be transmitted and detected. Many types of spectral sorters can replace any of the color filters 58, 61. Normally when light source 57 is a laser or diode, filter(s) 58 can be eliminated. After passing through filter 58 the light is focused onto fiber optic 6, for input to the reservoir FOCS, by lens 18. The output of the reservoir FOCS passes through lens 18 where it is collimated and passes through filter 61 at 90° to its face. The filtered light enters lens 18 and is brought to focus on detector 62. The electronics and optional electronics are the same as described for source/detector assembly 56, FIG. 15A, B. If source stabilization is to be used, detector 69 should be at the input of fiber optic 6 that transmits the light from the optical train to the FOCS, as shown in FIG. 16B.

As show in FIGS. 17A, B, C multiple reservoir FOCS are possible. FIG. 17A shows reservoir FOCS 83 is formed of two (2) modular reservoir cell bodies 1a, b joined together with a common membrane 3 at the interface therebetween. Channels 2 through the cell bodies are aligned and allow the sample to enter and leave the FOCS. The side of each channel 2 opposite to the common membrane 3 is covered with a membrane 3a, b. Membranes 3 and 3a, b can be the same or each can be of a different material. The membrane allows the sample(s) to be analyzed to enter the cells while keeping the species specific reagents 4 separated from each other and within their respective cells. The reagents 4 in each cell can of course be different. Retaining rings 5 hold outside membranes 3a, b in place and effect a liquid tight seal between cell body 1a, b and membranes 3a, b. Membrane 3 also makes a liquid tight seal between the faces of the two cell bodies. Fiber optics 6 are placed in cells 1a, b, one in each cell, through fiber optic mounts 7 which center fiber optics 6 within each cell body 1a, b. The fibers are oriented substantially normal to the flow direction which is transverse. The cell body makes water tight seals between the fiber optic 6 and the mount 7 as well as the mount 7 and the cell body 1a, b. The multi-cell reservoir FOCS, as assembled, encloses a predetermined volume in each cell which typically contains a known quantity of liquid reagent 4 within each of the cell bodies 1a, b. The measurement volume is defined by the numerical aperture of the fiber optic 6 and the geometry of channel 2. The desired chemical species permeate through membrane 3a into the first cell body 1a, interact with reagent 4, and produce an effect, e.g. fluorescence, absorption, reflection or refraction, which is detected by one fiber optic 6 in the first cell through the exposed tip 8 positioned in the cell body. The sample then passes through common membrane 3 into the second cell 1b and is detected by fiber tip 8 in the second cell. The detection apparatus and light sources required to operate the reservoir FOCS are known in the art and are shown schematically by source/detector assembly 56, FIG. 15 which is positioned at the other end of optical fiber 6 from reservoir FOCS 83. One (1) source/detector assembly 56 is needed for each cell 1a, b. FIG. 17B shows FOCS 84 the two (2) fiber optic/cell version of the multi-cell FOCS. FIG. 17C shows that it is possible to mix one (1) and two (2) fiber FOCS in a multi-cell system 85. FIG. 17D shows a two-cell system 86 in which the first cell is a reaction chamber and the second cell is the FOCS.

Figure 17E:
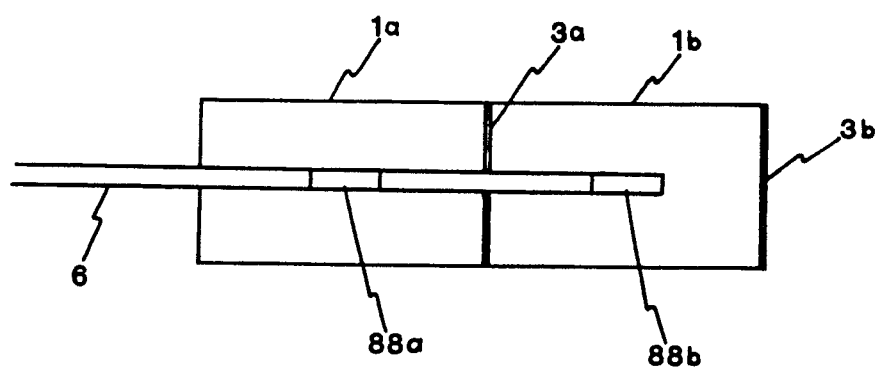
FIG. 17E shows a two-cell system with a single fiber optic extending through both cells.

The number of reaction chambers and the number of FOCS in a multi-cell system is limited only by the size and the chemistries. FIG. 17E shows another variation of a dual cell having a pair of cells 1a, b separated by a membrane 3a and an outer membrane 3b at the end of cell 1b opposite membrane 3a. A single fiber 6 extends through cell 1a and into cell 1b. Fiber 6 has a first reaction region 88a in cell 1a and a second reaction region 88b in cell 1b.

Figure 18A:
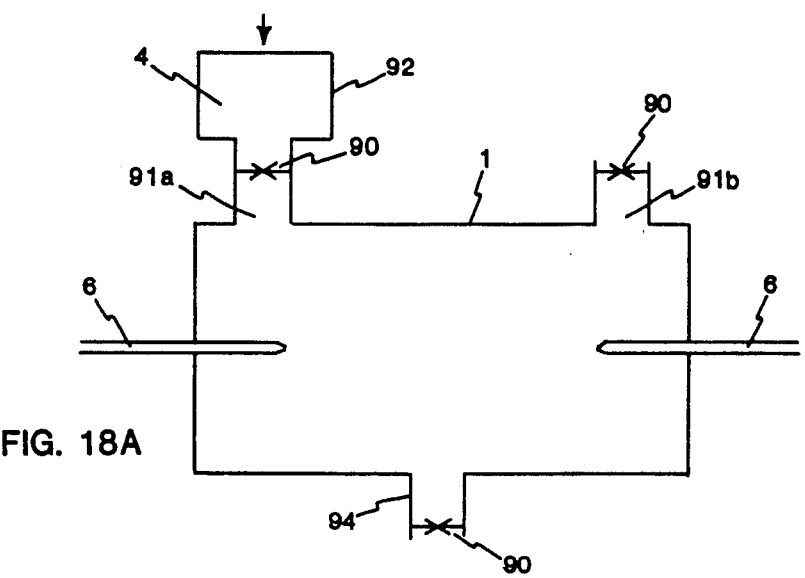
FIGS. 18A,B,C show continuous or pulsed replenishment reservoir FOCS.

Additional embodiments of the invention include continuous or pulsed reservoir FOCS as shown in FIGS. 18A, B, C. The embodiment of FIG. 18A has a single cell body 1 with a pair of optical fibers 6 positioned therein. Alternately, the invention can be implemented with either one or two fibers, also using any of the lens and/or mirror combinations of FIGS. 1A–F. The lateral membrane of FIGS. 1A–F is eliminated in the cell of FIG. 18A. The cross-flow through the cell body 1 is produced by lateral inlet ports 91a, b and lateral outlet port 94. An external reservoir 92 filled with reagent 4 is connected to inlet port 91a while inlet port 91b is used to input the sample, and the two are mixed in the cell. Outlet port 94 is used to remove the reagent/sample mixture while the cell is continuously replenished through inlet ports 91a, b. Valves 90 placed in the inlet and outlet ports regulate or control the flow. Suitable pumps can also be used. Pulsed flow operation is also possible. The flow is substantially transverse to the fiber optic. Fresh reagent and sample can be continuously flowed through the cell.

Figure 18B:
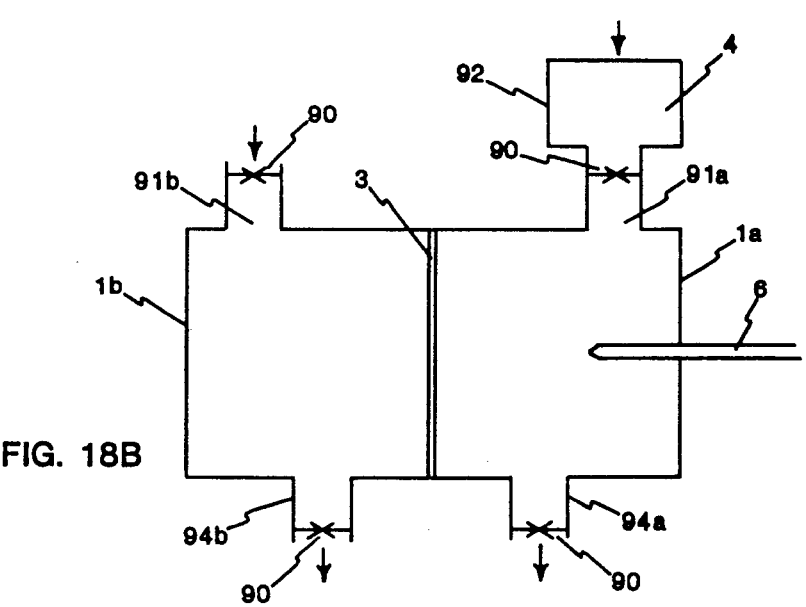
FIGS. 18B,C show two-cell designs separated by a membrane.

A two-cell configuration, as shown in FIG. 18B, has a first cell 1a and adjacent second cell 1b separated by a membrane 3. Fiber 6 extends into cell 1a. Reagent inlet port 91a inputs reagent 4 from external reservoir 92 into cell 1a while sample inlet port 91b inputs sample into cell 1b. The species of interest in the sample passes through membrane 3 into cell 1a and reacts with the reagent, producing an effect detected by optical fiber 6. Outlet ports 94a, b in cells 1a, b provide for flow out of cells 1a, b so the reagent and sample can be continuously replenished. Alternately pulsed operation can be used. Valves 90 in the inlet and outlet ports control flow.

Figure 18C:
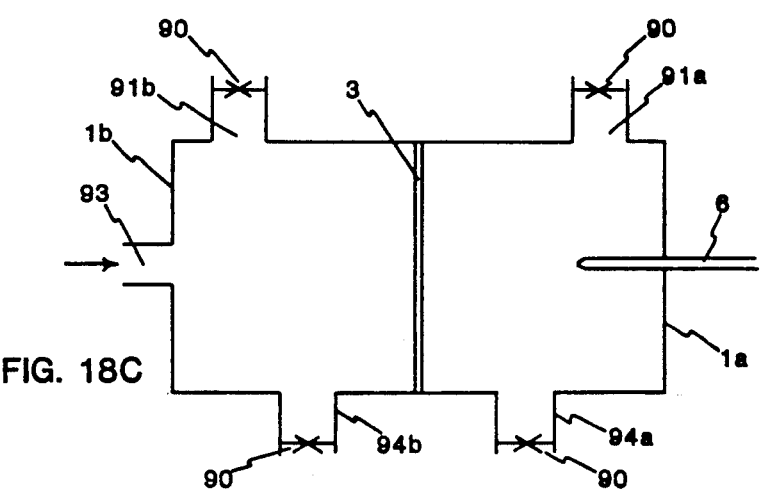

The two-cell embodiment of FIG. 18C is similar to FIG. 18B except that it includes an additional pressure port 93 in sample cell 1b. Pressure port 93 is used to pressurize the sample solutions in cell 1b to increase the flow rate of the species of interest through membrane 3 into reagent cell 1a. The flow through the membrane will depend on the pressure difference in the two cells. Valves 90 can also be used to control pressure in the cells.

The membrane is a very important part of the reservoir FOCS. It must perform several tasks simultaneously: (i) keep the sensing reagent in the FOCS, (ii) pass the species, or classes of compounds, of interest selectively and (iii) prevent potential interferences from getting into the FOCS. In the case of the reservoir FOCS, therefore, the membrane is defined as any material which separates the individual components of the sample from the FOCS so that reliable quantitative and qualitative measurements can be made. This separation may be accomplished by size, molecular weight, molecular charge, chemical reactions or combinations of these. Several reservoir FOCS have been based on size separation which is done with membranes of different pore size. This is the most common way to isolate gases and vapors from liquids. Separation of the components in one solution, i.e., the sensing reagent, from the species in a second solution, i.e., the sample, is most commonly done by molecular weight using a dialysis membrane. In situations where neither of these membranes work the options are: (i) put a charged surface on the membrane if the objective is to stop or pass a charged molecule, (ii) put a reactive surface on the membrane which will predictably convert the sample of interest to a species which will transport across the membrane or (iii) prepare the sample in the preparation chamber so that an acceptable species results. In many situations it is easier to work with the sensing reagent than the sample. The minimum hole size or molecular weight membrane that can be used is first defined by the conditions which allow the sample to enter the FOCS. If the sample does not reach the sensing reagent there can be no interaction. Under these conditions, sensing reagents may escape from the FOCS because they are smaller or of lower molecular weight than the sample. To overcome this problem the sensing reagent is reacted with a compound, such as an inert polymer, to increase its size and molecular weight. When adding to size or molecular weight of the sensing reagent, it is important not to block those chemical groups which specifically interact with the species of interest. In the same manner it is also possible to make a derivative of the sensing agent to give it specific properties, in addition to size and molecular weight, such as charge or additional species specific active groups.

The most commonly used measurement methods used with reservoir FOCS are: (i) fluorescence, (ii) absorption, (iii) chemiluminescence, (iv) refraction, (v) reflection, (vi) a combination of absorption and fluorescence and (vii) a combination of refraction and fluorescence. The reservoir FOCS designs according to the invention can be used with virtually any measurement method and indicator material, including virtually all fluorescer and absorber materials.

Fluorescence is a two (2) wavelength system-excitation at one wavelength and emission at another higher wavelength. In addition, many compounds are excited in the blue to ultraviolet wavelength range where the light energy is more energetic. In the general class of fluorescence sensors the light which is used to stimulate the fluorescer molecule generally causes photo-degradation or bleaching of that analyte molecule. This limits the intensity of light which may impinge on this molecule for a given sensor lifetime. The limited light intensity, in turn, limits the fluorescence signal which may be generated from a sample of fixed concentration because the fluorescence intensity is proportional to the excitation intensity. It is, therefore, desireable to use the lowest possible source intensity and it is of utmost importance to collect as much of the fluorescence signal as possible and process it optimally. Signal collection depends on the efficiency of the optical system. FOCS 11, 14, 19 show how this can be accomplished with the single fiber system using focusing mirror 12, diverging lens 15 or both. FOCS 17 shows how this can be done with a two (2) fiber optic system using collimating lenses 18. In addition, by using the optional electronic feed back circuits in source/detector assemblies 56, 82 and low noise components, particularly amplifiers, it is possible to process detector signals in the sub-nanowatt range and detect part-per-billion concentrations of most samples.

Absorption spectroscopy is a single wavelength method. Ideally, measurements are made at the same wavelength as the absorption maximum of the species being analyzed. From a practical point of view wavelengths under the absorption band are more than acceptable while wavelengths outside this region will still suffice. In general, since this is not an excitation process such as fluorescence, the sample colors are stable. In addition, absorption measurements are most often made in the visible area of the spectrum where the light is not as energetic as the ultraviolet. Concentrations in the low parts-per-billion range have been detected with a reservoir FOCS using absorption techniques.

Chemiluminescence does not have as broad a species coverage as fluorescence or absorption but is very useful for some key compounds. In chemiluminescence a room temperature reaction occurs between compounds that do not emit light to generate fluorescence or phosphorescence. This technique can be used in a FOCS in several ways: (i) to detect compounds which generate a unique emission, (ii) to measure biological materials such as bacteria (bioluminescence) and (iii) to analyze species which have specific catalytic effects on the excitation/emission process.

In some situations it is not possible to get a light source at the optimum wavelength, or if a source is available it may not be sufficiently intense or stable. In these situations a fluorophor which emits at the desired wavelength becomes a secondary light source for the measurement. Laser dyes, in particular, make good sources for absorption measurements because they cover the visible spectral region in overlapping increments. By using an excess of fluorophor, the effects of photobleaching are obviated even over extended analysis times. The fluorophor can either be immobilized on the fiber or put into the sensing solution (if the sensing solution and fluorophor are chemically compatible). Changes in the amount of fluorescence can be related to sample concentration.

In those circumstances where the sample is colorless, it is possible to make refraction measurements using a fluorophor immobilized on the fiber. In this case it is not possible to mix the fluorophor with the sample because this would add color and make it impossible to distinguish between absorption and refraction. The light intensity received by the sensor varies with the refractive index of the sample and can be used to measure the amount of species present. This technique can be used for liquid, vapor or gas samples. In the case of a liquid sample the fluid inside the FOCS can be the same as the sample if impurities are the analytical target. If the liquid itself is to be measured then a solvent is placed in the FOCS. If part of a liquid sample is to be analyzed the solvent in the FOCS is chosen so that the species of interest partition into the FOCS. Vapors and gases can cross directly into the FOCS and be measured or they can be dissolved in a calibrated solvent and analyzed.

Although the reservoir FOCS is primarily a qualitative and quantitative monitoring device for pollutants and trace species in air, sweet water and sea water, this type of efficient, small size, simple measurement system has many uses. These applications include: (i) simplified fluorescence and absorption spectrometers for testing laboratories, (ii) absorption detection units for high pressure liquid chromatography (HPLC) where the difficulties of designing detector cells using bulk optics are substantial, (iii) flow cells for flow injection and continuous flow analyzers, (iv) small sampling heads for process stream analyzers in production facilities, (v) determination of cell population in biological broths and (vi) in-vitro measurement of species of medical interest. In each of these areas the FOCS allows the optical sampling cell to be placed at some location which is optimized for the analysis rather than at a location which is optimized for bulk optics placement. Thus, connecting flow tubes to the cell can be minimized, in turn, minimizing dead volume and analyte band broadening.

One specific type of reservoir FOCS is a pH sensor. The pH FOCS is formed using a hydrogen ion/hydronium ion ($H^+/H_3O^+$) permeable membrane and the reservoir cell is filled with a reagent solution which reacts with hydrogen ion/hydronium ion which permeates through the membrane. The cell is illuminated by an input or excitation signal through the fiber optic and an output signal is produced whose intensity can be related to pH.

Absorption and luminescence quenching are the bases for the reservoir cell pH sensor. Several pH sensitive absorption dyes such as phenol red, cresol red, methyl violet, congo red, phenolphthalein, and bromcresol purple can be used in absorption or in fluorescence in conjunction with a pH insensitive fluorophor such as eosin. Either of these techniques are applicable to all dyes that change color as a function of pH. Dye concentrations are $10^{-2}$ molar while the eosin is $>10^{-4}$ molar. Direct fluorescence measurements using fluorescein, acridine, umbelliferone and beta-naphthol at between $10^{-4}$ and $10^{-5}$ molar can also be used if excitation power can be kept below the photodecomposition level. A reagent solution of either of these types of reagents can be placed in the reservoir cell. A dialysis membrane of MWCO (molecular weight cut off) 100 is used to keep the reagents in the cell while passing the hydrogen ion/hydronium ion. For the absorption dyes eosin can be excited at 488 nm and its emission peak appears at 566 nm. This is an ideal wavelength range to work in. Phenol red covers pH range 6.8 to 8.4, cresol red 7.2 to 8.8, methyl violet 0.1 to 1.5, congo red 3.0 to 5.2, phenolphthalein 8.2 to 10.0 and bromocresol purple 5.2 to 6.8. Either the single or two (2) FOCS design can be used for absorption measurements. Fluorescein is an example of a fluorescent dye. It can be excited at 488 nm and it emission peak is at 545 nm. In solution fluorescein responds to pH range 4.0 to 6.8. Single fiber optic systems work best with fluorescence. This technique is applicable to all pH sensitive dyes which change color or fluoresce.

Another specific type of reservoir FOCS is an arsenic sensor. The arsenic FOCS is formed using an arsenic ion permeable membrane and the reservoir cell is filled with a reagent solution which reacts with the arsenic ion. The arsenic ion permeates through the membrane. The cell is illuminated by an excitation signal through the fiber optic and an output signal is produced whose intensity can be related to arsenic ion concentration.

Absorption or luminescence quenching is the basis for the reservoir cell arsenic ion sensor. A reagent solution of either ammonium molybdate and stannous chloride or N-ethyl-8-hydroxtetrahydroquinoline and ferric chloride can be placed in the reservoir cell. A dialysis membrane of MWCO (molecular weight cut off) 100 is used to keep the reagents in the cell while passing the arsenic ion. The ammonium molybdate/stannous chloride gives a blue color with arsenic ion whose intensity is dependent on arsenic concentration. This is measured in absorption at 450 nm. The N-ethyl-8-hydroxtetrahydroquinoline/ferric chloride gives a red-brown color with arsenic ion and is detected in absorption at 600 nm. These reactions can also be measured in fluorescence by using eosin immobilized on a fiber optic inserted into the cell and exciting at 488 nm and detecting at 546 nm. The loss of fluorescence intensity at the detector due to color formation can be related to arsenic concentration. Both the ammonium molybdate/stannous chloride and N-ethyl-8-hydroxtetrahydroquinoline/ferric chloride solution have limited shelf-lives. To improve this the individual components of the solution are separated into a two-cell FOCS, FIG. 17D. The arsenic solution, in this configuration, first enters the ammonium molybdate solution and reacts. The resultant product, arsenomolybdate, then passes through the second membrane into the second cell where the stannous chloride is stored. When this happens the blue color is formed. This can also be done with the N-ethyl-8-hydroxtetrahydroquinoline in the first cell and the ferric chloride in the second.

Another specific type of reservoir FOCS is a benzene sensor. The benzene FOCS is formed using a benzene permeable membrane. Care has to be taken that this membrane does not dissolve or lose its separative properties in benzene. The reservoir cell is filled with a solvent for benzene whose refractive index is much smaller than benzene. Benzene permeates through the membrane and is collected in the solvent. The cell is illuminated by an excitation signal through the fiber optic and an output signal is produced whose intensity can be related to benzene concentration.

Benzene is determined using a combination of refractive index and fluorescence. The FOCS is filled with a compound with a lower refractive index than benzene (refractive index 1.50) in which benzene is soluble, e.g., ethanol (refractive index 1.36) or acetone (refractive index 1.36). The benzene permeable, benzene/solvent insoluble membrane is a polymer, e.g., high density polyethylene, high density polypropylene or fluorinated or surface fluorinated forms of these). The fiber optic is coated with a fluorophor immobilized in a benzene insoluble matrix. The signal obtained for pure solvent is used as the baseline. As benzene dissolves in the solvent the refractive index of the solvent increases, changing its light transmission characteristics. The differences in the intensity of light signal received at the detector between the baseline (pure solvent) measurement and the solvent containing benzene can be related to benzene concentration.

Another specific type of reservoir FOCS is a cyanide sensor. The cyanide FOCS is formed using a cyanide permeable membrane and a sensing reagent specific to cyanide. Cyanide permeates through the membrane and is collected in a solution of the species specific sensing reagent. The cell is illuminated by an excitation signal through the fiber optic and an output signal is produced whose intensity can be related to cyanide concentration.

Cyanide is determined using luminescence. The FOCS is filled with p-benzoquinone which specifically reacts with cyanide to form 2,3-dicyanoquinone. The benzoquinone is held in the FOCS with a membrane of MWCO 100. Luminescence excitation is at 450 nm and emission is at 500 nm. The fluorescence of the benzoquinone changes its light transmission characteristics. The differences in the intensity of light signal received at the detector between the base line (p-benzoquinone) measurement and the increase in fluorescence as the 2,3-dicyanoquinone is formed can be related to cyanide concentration.

Another specific type of reservoir FOCS is a hydrazine sensor. The hydrazine FOCS is formed using a hydrazine permeable membrane and a sensing reagent specific to hydrazine. Hydrazine permeates through the membrane and is collected in a solution of the species specific sensing reagent. The cell is illuminated by an excitation signal through the fiber optic and an output signal is generated whose intensity can be related to hydrazine concentration.

Hydrazine is determined using absorpotion. The FOCS is filled with cupric neocuproine solution which specifically reacts with hydrazine to form a yellow solution. The more hydrazine the darker the solution. The cupric neocuproine is held in the FOCS with a membrane of MWCO 100. The absorption of light at 450 to 458 nm in pure neocuproine is used as a baseline. More absorption occurs as hydrazine enters the FOCS. The increase in absorption can be related to hydrazine concentration.

Another specific type of reservoir FOCS is a cupric ion sensor. The copper FOCS is formed using a cupric ion permeable membrane and a sensing reagent specific to copper. Cupric ion permeates through the membrane and is collected in a solution of the species specific sensing reagent. In one (1) embodiment of the copper sensor the sample is excited by light propagating through the fiber optic while in a second system the reaction of the sample with the reagent generates light. An output singal is generated whose intensity can be related to copper concentration.

Cupric ion is determined using either fluorescence or chemiluminescence. In one system the FOCS is filled with 2,2'-dipyridylketone hydrazone solution which specifically reacts with copper. The 2,2'-dipyridylketone hydrazone solution is held in the FOCS with a membrane of MWCO 100. The fluorescence of the 2,2'-dipyridylketone hydrazone is quenched by copper in a manner which can be directly related to cupric ion concentration. In another approach the FOCS is filled with lumocupferron solution. This is kept in the FOCS with a membrane of MWCO 100. Copper specifically catalyzes the chemiluminescence of lumocupferron. The intensity of the self-emitting light can be directly related to copper concentrations. One of the advantages of this chemiluminescence reaction is its sensitivity, <1 ppb.

Another specific type of reservoir FOCS is a Trichloroethylene (TCE) sensor. The TCE FOCS is formed using a TCE permeable membrane. Care has to taken that this membrane does not dissolve or lose its separative properties in TCE. The reservoir cell is filled with a solvent for TCE whose refractive index is much smaller than TCE. TCE permeates through the membrane and is collected in the solvent. The cell is illuminated by an excitation signal through the fiber optic and an output signal is produced whose intensity can be related to TCE concentration.

TCE is determined using a combination of refractive index and fluorescence. The FOCS is filled with compound with a lower refractive index than TCE (refractive index 1.48) in which TCE is soluble, e.g., ethanol (refractive index 1.36) or acetone (refractive index 1.36). The TCE permeable, TCE/solvent insoluble membrane is a silicone polymer. These are chosen because they selectively pass chlorinated hydrocarbons thus adding specificity to the analysis. The fiber optic is coated with a fluorophore immobilized in a TCE insoluble matrix. The signal obtained for pure solvent is used as the baseline. As TCE dissolves in the solvent the refractive index of the solvent increases changing its light transmission characteristics. The differences in the intensity of light signal received at the detector between the baseline (pure solvent) measurement and the solvent containing TCE can be related to TCE concentration.

Another specific type of reservoir FOCS is a mercuric ion sensor. The mercury FOCS is formed using a mercuric ion permeable membrane and a sensing reagent specific to mercury. Mercuric ion permeates through the membrane and is collected in a solution of the species specific sensing reagent. In the mercury sensor, the sample is excited by light propagating through the fiber optic and an output signal is generated whose intensity can be related to mercury concentration.

Mercuric ion is determined using "heavy metal" fluorescence quenching. In one system, the FOCS uses 2,2'-dipyridylketone hydrazone solution which specifically reacts with mercury. The 2,2'-dipyridylketone hydrazone solution is held in the FOCS with a membrane of MWCO 500. The fluorescence of the 2,2'-dipyridylketone hydrazone is quenched by mercury in a manner which can be directly related to mercuric ion concentration. Since many metals quench 2,2'-dipyridylketone hydrazone, its specificity is obtained by proper selection of the excitation and emission wavelengths. The decrease in fluorescence intensity can be directly related to mercuric ion concentration. Another mercuric specific reagent is indole-3-propionic acid. This is also kept in the FOCS with membrane of MWCO 500. Mercury predictably quenches the fluorescence of indole-3-propionic acid so that the intensity of the light emission can be equated to mercuric ion concentration.

Another specific type of reservoir FOCS is an iron(2+) sensor. The iron(2+) FOCS is formed using an iron(2+) permeable membrane and a sensing reagent specific to iron(2+). Iron(2+) permeates through the membrane and is collected in a solution of the species specific sensing reagent. In the iron(2+) sensor, light enters the sample through an optical fiber, interacts with the sample, and an output signal is generated whose intensity can be related to iron(2+) concentration.

Iron(2+) is determined using absorption. The FOCS uses ferrozine solution which specifically reacts with iron(2+). It does not respond to iron(3+). Ferrozine is very light yellow in solution. It turns various densities of purple when exposed to different concentrations of iron(2+). The ferrozine is kept in the FOCS with membranes of either MWCO 100 or 500. The ferrozine absorbs the input light in a predictable manner so that light loss, or the percent of light absorbed, can be used to determine iron(2+) concentration. At low ppm and ppb iron(2+) concentration, light intensity is linear with iron(2+) concentrations.

The above-described preferred embodiments of the invention are not intended to be exhaustive of all possible reservoir FOCS cells. In accordance with the invention, different reservoir FOCS can be designed which are specific to a wide number of particular species, using any known fluorescer or absorber or other known detection mechanism which can be carried out in a FOCS.

Changes and mocifications in the specifically described embodiments can be carried out without departing from the scope of the invention which is intended to be limited only by the scope of the appended claims.

We claim:

1. A reservoir cell fiber optic chemical sensor, comprising:
   a modular cell body with a fluid communication opening on a lateral face thereof;
   a semipermeable membrane mounted on the lateral face and covering the fluid communication opening;
   a sensing reagent filling the cell body and contained therein by the membrane;
   a fiber optic connected to one end of the modular cell body and oriented substantially transversely to the direction of flow of chemical species through the membrane;
   wherein the membrane and sensing reagent are selected from the following combinations:
   (a) the membrane is a hydrogen ion/hydronium ion permeable membrane and the sensing reagent is selected from pH sensitive absorption dyes and pH sensitive fluorescent dyes;
   (b) the membrane is an arsenic ion permeable membrane and the sensing reagent is selected from an ammonium molybdate/stannous chloride mixture and an N-ethyl-8-hydroxtetrahydroquinoline/ferric chloride mixture;
   (c) the membrane is selected from high density polyethylene, high density polypropylene and fluorinated forms thereof, and the sensing reagent is a solvent for benzene with refractive index lower than benzene;
   (d) the membrane is a cyanide permeable membrane and the sensing reagent is p-benzoquinone;
   (e) the membrane is a hydrazine permeable membrane and the sensing reagent is cupric neocuproine solution;
   (f) the membrane is a cupric ion permeable membrane and the sensing reagent is selected from 2,2'-dipyridylketone hydrazone solution and lumocupferron solution;
   (g) the membrane is a TCE permeable silicone polymer and the sensing reagent is a solvent for TCE with refractive index lower than TCE;
   (h) the membrane is a mercuric ion permeable membrane and the sensing reagent is selected from 2,2'-dipyridylketone hydrazone solution and indole-3-propionic acid;
   (i) the membrane is an iron(2+0 permeable membrane and the sensing reagent is ferrozine solution.

2. The cell of claim 1 further comprising a diverging lens attached to the tip of the fiber optic.

3. The cell of claim 1 further comprising a focusing mirror positioned in the cell body at an opposed end from the fiber optic.

4. The cell of claim 2 further comprising a focusing mirror positioned in the cell body at an opposed end from the fiber optic.

5. The cell of claim 1 further comprising a second fiber optic connected to an opposed end of the cell body from the other fiber optic.

6. The cell of claim 5 further comprising a collimating lens attached to each fiber optic.

7. The cell of claim 1 wherein the cell body comprises an open tube and the fluid communication opening comprises a pair of opposed ports on the lateral surface of the tube.

8. The cell of claim 7 wherein one end of the tube is threaded and the fiber optic is connected to the tube by a mating connector which engages the threaded end of the tube.

9. The cell of claim 8 wherein the opposite end of the tube is threaded and further comprising a second fiber optic connected by a second mating connector to the opposite end of the tube.

10. The cell of claim 1 wherein the cell body comprises a substantially rectangular shaped cell body having a channel extending therethrough between two opposed faces and a membrane is mounted on each of the two opposed faces.

11. The cell of claim 2 wherein the diverging lens is mounted in an end wall of the cell.

12. The cell of claim 1 further comprising a sample preparation chamber adjacent to the modular cell body and having the semi-permeable membrane as an interface between the sample preparation chamber and cell body.

13. The cell of claim 12 wherein the cell body has a second membrane on an opposed face from the interface with the sample preparation chamber.

14. The cell of claim 12 wherein the sample preparation chamber has an inlet port and outlet port for passing sample through the chamber and an irradiation port for irradiating the sample in the chamber.

15. The cell of claim 14 further comprising a second inlet port in the chamber for introducing reactant chemical species.

16. The cell of claim 12 further comprising a chemical bed in the chamber.

17. A multiple reservoir fiber optic chemical sensor, comprising first and second reservoir cell bodies arranged adjacent to each other and defining a flow channel therethrough;
a first semi-permeable membrane at the interface between the first and second cell bodies;
a second and third semi-permeable membrane on the opposite ends of the first and second cell bodies from the cell interface, respectively, and covering the ends of the flow channel;
a sensing reagent in each cell body;
at least one fiber optic extending into at least one cell body and oriented in a direction substantially orthogonal to the flow channel.

18. A continuous or pulsed replenishment reservoir fiber optic chemical sensor, comprising:
a reservoir cell body;
reagent inlet means in the cell body;
sample inlet means in the cell body;
outlet means in the cell body;
an optical fiber connected to the cell body.

19. The cell of claim 18 further comprising a semipermeable membrane dividing the cell body into a sample chamber and reaction chamber with the fiber optic and reagent inlet means in the reaction chamber, the sample inlet means in the sample chamber, and outlet means in both chambers.

20. A reservoir fiber optic chemical sensor comprising:
an inner sleeve having a plurality of holes therein;
a semi-permeable membrane wrapped around the lateral surface of the inner sleeve;
an outer sleeve having a plurality of holes therein and surrounding the inner sleeve;
a first end cap sealing one end of the concentric sleeves;
a second end cap sealing the other end of the concentric sleeves;
a sensing reagent filling the inner sleeve and contained therein by the membrane and end caps;
a fiber optic connected to the first end cap.

21. The sensor of claim 20 further comprising a second fiber optic connected to the second end cap.

22. The sensor of claim 20 further comprising a plurality of spacers separating the first and second sleeves.

23. The sensor of claim 20 for measuring pH wherein the membrane is a hydrogen ion/hydronium ion permeable membrane and the sensing reagent is selected from pH sensitive absorption dyes and pH sensitive fluorescent dyes.

24. The sensor of claim 23 wherein the absorption dye is selected from phenol red, cresol red, methyl violet, congo red, phenolphthalein and bromcresol purple.

25. The sensor of claim 24 wherein the absorption dye is used in conjunction with a pH insensitive fluorophore.

26. The sensor of claim 25 wherein the fluorophore is eosin.

27. The sensor of claim 23 wherein the fluorescent dye is selected from fluorescein, acridine, umbelliferone, and beta-naphthol.

28. The sensor of claim 20 for arsenic wherein the membrane is an arsenic ion permeable membrane and the sensing reagent is selected from an ammonium molybdate/stannous chloride mixture and an N-ethyl-8-hydroxtetrahydroquinoline/ferric chloride mixture.

29. The sensor of claim 17 wherein the first cell body is filled with ammonium molybdate solution and the second cell body is filled with stannous chloride solutions, and the sensor has a fiber optic connected to the second cell body.

30. The sensor of claim 17 wherein the first cell body is filled with N-ethyl-8-hydroxtetrahydroquinoline and the second cell is filled with ferric chloride solution, and the sensor has a fiber optic connected to the second cell body.

31. The sensor of claim 20 for benzene wherein the membrane is selected from high density polyethylene, high density polypropylene and fluorinated forms thereof, and the sensing reagent is a solvent for benzene with refractive index lower than benzene.

32. The sensor of claim 20 for cyanide wherein the membrane is a cyanide permeable membrane and the sensing reagent is p-benzoquinone.

33. The sensor of claim 20 for hydrazine wherein the membrane is a hydrazine permeable membrane and the sensing reagent is cupric neocuproine solution.

34. The sensor of claim 20 for cupric ion wherein the membrane is a cupric ion permeable membrane and the sensing reagent is selected from 2,2'-dipyridylketone hydrazone solution and lumocupferron solution.

35. The sensor of claim 20 for TCE wherein the membrane is a TCE permeable silicone polymer and the sensing reagent is a solvent for TCE with refractive index lower than TCE.

36. The sensor of claim 35 wherein the solvent is ethanol or acetone.

37. The sensor of claim 20 for mercuric ion wherein the membrane is a mercuric ion permeable membrane and the sensing reagent is selected from 2,2'dipyridylketone hydrazone solution and indole-3-propionic acid.

38. The sensor of claim 20 for iron(2+) wherein the membrane is an iron(2+) permeable membrane and the sensing reagent is ferrozine solution.

* * * * *